(12) United States Patent
Skeiky et al.

(10) Patent No.: US 7,064,195 B2
(45) Date of Patent: Jun. 20, 2006

(54) FUSION PROTEINS OF MYCOBACTERIUM TUBERCULOSIS ANTIGENS AND THEIR USES

(75) Inventors: Yasir Skeiky, Bellevue, WA (US); Mark Alderson, Bainbridge Island, WA (US); Antonio Campos-Neto, Bainbridge Island, WA (US)

(73) Assignee: Corixa, Seattle, WA (US)

( * ) Notice: Subject to any disclaimer, the term of this patent is extended or adjusted under 35 U.S.C. 154(b) by 123 days.

(21) Appl. No.: 10/359,459

(22) Filed: Feb. 5, 2003

(65) Prior Publication Data

US 2004/0013677 A1 Jan. 22, 2004

Related U.S. Application Data

(63) Continuation of application No. 09/223,040, filed on Dec. 30, 1998, now Pat. No. 6,544,522.

(51) Int. Cl.
*C07H 21/04* (2006.01)
*C07H 21/02* (2006.01)
*A61K 39/04* (2006.01)

(52) U.S. Cl. ............... 536/23.7; 424/9.2; 424/130.1; 424/164.1; 424/168.1; 424/190.1; 424/248.1; 435/69.1; 435/69.3; 514/44; 530/350; 536/23.1

(58) Field of Classification Search ............. 424/9.2, 424/130.1, 164.1, 168.1, 190.1, 248.1; 435/69.1, 435/69.3; 514/44; 530/350; 536/23.1, 23.7
See application file for complete search history.

(56) References Cited

U.S. PATENT DOCUMENTS

5,330,754 A 7/1994 Kapoor et al. ........... 424/190.1

FOREIGN PATENT DOCUMENTS

| WO | WO 95/01440 | 1/1995 |
| WO | WO 95/14713 | 6/1995 |
| WO | WO 97/09428 | 3/1997 |
| WO | WO 97/09429 | 3/1997 |

OTHER PUBLICATIONS

Philipp et al., An integrated map of the genome of the tubercle bacillus *Mycobacterium tuberculosis* H37Rv, and comparison with *Mycobacterium leprae, Proc. Natl. Acad. Sci*, 93:3132-3137 (1996).

Lee et al., Characterization of the Major Membrane Protein of Virulent *Mycobacterim tuberculosis, Infection and Immunity*, p. 2066-2074 (May 1992).

Pal et al., "Immunization with Extracellular Proteins of *Mycobacterium tuberculosis* Induces Cell-Mediated Immune Responses and Substantial Protective Immunity in a Guinea Pig Model of Pulmonary Tuberculosis"; *Infection and Immunity* vol. 60, No. 11, pp. 4781-4792 (Nov. 1992).

*Primary Examiner*—Rodney P Swartz
(74) *Attorney, Agent, or Firm*—Townsend and Townsend and Crew LLP

(57) ABSTRACT

The present invention relates to fusion proteins of *Mycobacterium tuberculosis* antigens. In particular, it relates to two fusion proteins, each of which contains three individual *M. tuberculosis* antigens, and a fusion protein of two *M. tuberculosis* antigens, their coding sequences, and methods for their use in the treatment and prevention of tuberculosis.

9 Claims, 21 Drawing Sheets

FIG. 1A

FIG. 1B

Figure 3A:
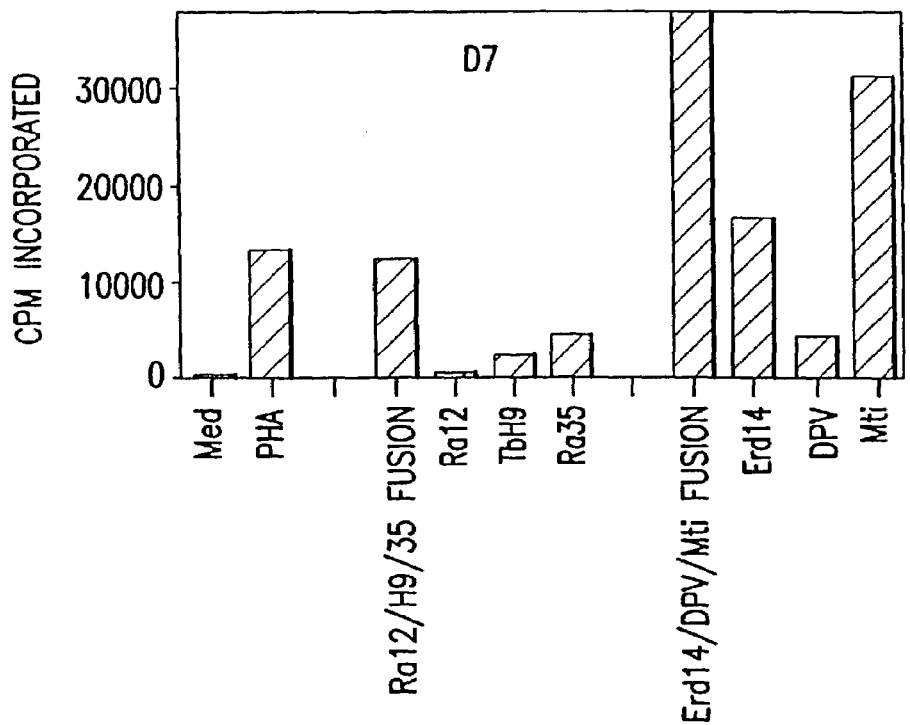

```
GGTCGGGTATGACCGCACCCAGGATGTCGCGGTGCTGCAGCTGCGCGGTGCCGGTGCGCGGCGATCGGTGGCGGTCGCGGTTG  1995
 V  G  Y  D  R  T  Q  D  V  A  V  L  Q  L  R  G  A  G  G  L  P  S  A  A  I  G  G  G  V  A  V
|------------------------------------Tb Ra35----------------------------------------|
GTGACCCCTTCGTCGCGATGGGCAACAGCGGTGGGCAGGGCGGAACGCCCCGTGCCTGGCGGTGTCCGGCGCTGCAGGTGTCGCCAAACCGTGCAG  2090
 G  E  P  F  V  A  M  G  N  S  G  G  Q  G  G  T  P  R  A  V  P  G  R  V  V  A  L  G  Q  T  V  Q
|------------------------------------Tb Ra35----------------------------------------|
GCGTCGGATTCGGCTGACCGGTGCCGAAGAGACATTGAACGGGTTGATCCAGTTCGATGCCGGTGATTCGGGGGGCCCGTCGT  2185
 A  S  D  S  L  T  G  A  E  E  T  L  N  G  L  I  Q  F  D  A  A  I  Q  P  G  D  S  G  G  P  V  V
|------------------------------------Tb Ra35----------------------------------------|
CAACGGGCCTAGGACAGGTGGTCGGTATGAACACGGCCGTCCTAGGATATCCATCACACTGGCGGCCGCTCGAGCAGATCCGGNTGTAACAAAG  2280
 N  G  L  G  D  V  V  G  M  N  T  A  A  S   >
|------------Tb Ra35-----------|
```

FIG. 1C (CONTINUED FROM FIG. 1B)

```
GATATACATATGCATCACCATCACCATCACATGGCCACCACCCTTCCCGTTCAGGCCACCCGCGGTCCCTCTTCCCGGAGTTTCTGAGCTGTT  095
              M  H  H  H  H  H  H  M  A  T  T  L  P  V  D  R  H  P  R  S  L  F  P  E  F  S  E  L  F
                                                             |------ERD 14------
CGGGGCCTTCCCGTCATTCGCCGACTCCGGCCACCTTCGACACCCGGTTGACGGCGGTTGAAGACGATGAAAGAGGGCGCTACGAGGTAC  190
 A  A  F  P  S  F  A  G  L  R  P  T  F  D  T  R  L  M  R  L  E  D  E  M  K  E  G  R  Y  E  V
-----ERD 14-----

GCGGGGAGCTTCCCGGGGTCGACAAGGACGTCGACATTATGGTCCGCGATGGTCAGCTGACCATCAAGGCCGAGCGCACCGAGCAGAAG  285
 R  A  E  L  P  G  V  D  P  D  K  D  V  D  I  M  V  R  D  G  Q  L  T  I  K  A  E  R  T  E  Q  K
-----ERD 14-----

GACTTCGACGGTCGCTCGGAATTCGCTTACGGTTCCTTCGTTCGCACGGTGTCGCTGCCGGTAGGTGCTGACGAGGACGACATTAAGGCCACCTA  380
 D  F  D  G  R  S  E  F  A  Y  G  S  F  V  R  T  V  S  L  P  V  G  A  D  E  D  D  I  K  A  T  Y
-----ERD 14-----

CGACAAGGGCATTCTTACTGTGTCGGTGGCGTTTCGGAAGGAAGCCAACCGAAAAGCACATTCAGATCCGGTCCACCAACAAGCTTGATCCCG  475
 D  K  G  I  L  T  V  S  V  A  V  S  E  G  K  P  T  E  K  H  I  Q  I  R  S  T  N  K  L  D  P
-----ERD 14-----                                                      |HindII|--DPV--

TGGACGCGGTCATTAACACACTGCAATTCAACGGGCAGTAGCTGCGCTCAACGCGACGATCCGGGGCCGCACAGTTCAACGCCTCA  570
 W  D  A  V  I  N  T  T  C  N  Y  G  Q  V  V  A  A  L  N  A  T  D  P  G  A  A  A  Q  F  N  A  S
----DPV----

CGAGTGACCTGTTTTCGGCCGCGTCGGAGTCGTTCAGTCGGCGTTCAGTCGGGGTCTGACGGTGGGGTCGTGGATAGTTCGTCGGCCGTCGTGATGGTG  665
 P  V  A  D  S  Y  L  R  N  F  L  A  A  P  P  P  Q  R  A  A  M  A  A  O  L  O  A  V  P  G  A  A
---DPV---

ACAGTACATCGGCCTTGTCGTCGAGTCGGTTGCCGAGTCGGTTGCCGACAACTATGAGCTCATGACGATTAATTACCAGTTCGGGGACGCTCATG  760
 Q  Y  I  G  L  V  E  S  V  A  G  S  C  N  N  Y  E  L  M  T  I  N  Y  Q  F  G  D  V  D  A  H
----DPV----                          |SacI|            ---MTI---

GCGCCATGATCCGCGCTCAGGCGGCGTCGCTTGAGGCGGAGCATCAGGCGCCATCGTTCGTGATGTGTTGGCCGCGGGTGACTTTTGGGGCGGCGCC  855
 G  A  M  I  R  A  O  A  A  S  L  L  E  A  E  H  Q  A  I  V  R  D  V  L  A  A  G  D  F  W  G  G  A
                                                                           ---MTI---

GGTTCGGTGGCTTGCCAGGAGTTCATTACCCAGTTGGGCCGTGATCTGGGCCGTAACTTCCAGTTCCAAGTTTATTGAGCAGAATCGGCAGGC  950
 G  S  V  A  C  Q  E  F  I  T  Q  L  G  R  N  F  Q  V  I  Y  E  Q  A  N  A  H  G  Q  K  V  Q  A
                                                           ---MTI---
```

FIG. 2A

TGCCGGCAACAACATGGCGCAAACCGACAGCGCCGTCGGCTCCAGCTGGGCCACTAGTAACGGCCGCCAGTGTGCTGGAATTCTGCAGATATCCA 1045
 A  G  N  N  M  A  Q  T  D  S  A  V  G  S  S  W  A  [Spe I]
------------MTI-------------------------------------(
TCACACTGGCGGGCCGCTCGAGCAGATCCGGCTGCTA 1081

FIG. 2B (CONTINUED FROM FIG. 2A)

US 7,064,195 B2

FUSION PROTEINS OF MYCOBACTERIUM TUBERCULOSIS ANTIGENS AND THEIR USES

This application is a continuation of Ser. No. 09/223,040 filed Dec. 30, 1998 now U.S. Pat. No. 6,544,522.

1. INTRODUCTION

The present invention relates to fusion proteins of *Mycobacterium tuberculosis* antigens. In particular, it relates to two fusion proteins, each of which contains three individual *M. tuberculosis* antigens, and a fusion protein of two *M. tuberculosis* antigens, their coding sequences, and methods for their use in the treatment and prevention of tuberculosis invention.

2. BACKGROUND OF THE INVENTION

Tuberculosis is a chronic infectious disease caused by infection with *M. tuberculosis*. It is a major disease in developing countries, as well as an increasing problem in developed areas of the world, with about 8 million new cases and 3 million deaths each year. Although the infection may be asymptomatic for a considerable period of time, the disease is most commonly manifested as an acute inflammation of the lungs, resulting in fever and a nonproductive cough. If untreated, serious complications and death typically result.

Although tuberculosis can generally be controlled using extended antibiotic therapy, such treatment is not sufficient to prevent the spread of the disease. Infected individuals may be asymptomatic, but contagious, for some time. In addition, although compliance with the treatment regimen is critical, patient behavior is difficult to monitor. Some patients do not complete the course of treatment, which can lead to ineffective treatment and the development of drug resistance.

In order to control the spread of tuberculosis, effective vaccination, and accurate early diagnosis of the disease are of utmost importance. Currently, vaccination with live bacteria is the most efficient method for inducing protective immunity. The most common Mycobacterium employed for this purpose is *Bacillus* Calmette-Guerin (BCG), an avirulent strain of *M. bovis*. However, the safety and efficacy of BCG is a source of controversy and some countries, such as the United States, do not vaccinate the general public with this agent.

Diagnosis of tuberculosis is commonly achieved using a skin test, which involves intradermal exposure to tuberculin PPD (protein-purified derivative). Antigen-specific T cell responses result in measurable induration at the injection site by 48–72 hours after injection, which indicates exposure to Mycobacterial antigens. Sensitivity and specificity have, however, been a problem with this test, and individuals vaccinated with BCG cannot be distinguished from infected individuals.

While macrophages have been shown to act as the principal effectors of *M. tuberculosis* immunity, T cells are the predominant inducers of such immunity. The essential role of T cells in protection against *M. tuberculosis* infection is illustrated by the frequent occurrence of *M. tuberculosis* in Acquired Immunodeficiency Syndrome patients, due to the depletion of $CD4^+$ T cells associated with human immunodeficiency virus (HIV) infection. Mycobacterium-reactive $CD4^+$ T cells have been shown to be potent producers of gamma-interferon (IFN-γ), which, in turn, has been shown to trigger the anti-mycobacterial effects of macrophages in mice. While the role of IFN-γ in humans is less clear, studies have shown that 1,25-dihydroxy-vitamin D3, either alone or in combination with IFN-γ or tumor necrosis factor-alpha, activates human macrophages to inhibit *M. tuberculosis* infection. Furthermore, it is known that IFN-γ stimulates human macrophages to make 1,25-dihydroxy-vitamin D3. Similarly, interleukin-12 (IL-12) has been shown to play a role in stimulating resistance to *M. tuberculosis* infection. For a review of the immunology of *M. tuberculosis* infection, see Chan and Kaufmann, 1994, *Tuberculosis: Pathogenesis, Protection and Control*, Bloom (ed.), ASM Press, Washington, D.C.

Accordingly, there is a need for improved vaccines, and methods for preventing and treating tuberculosis.

3. SUMMARY OF THE INVENTION

The present invention relates to fusion proteins of *M. tuberculosis* antigens. In particular, it relates to fusion polypeptides that contain two or three *M. tuberculosis* antigens, polynucleotides encoding such polypeptides, methods of using the polypeptides and polynucleotides in the treatment and prevention of *M. tuberculosis* infection.

The present invention is based, in part, on Applicants' discovery that two polynucleotides, each containing three *M. tuberculosis* coding sequences, produced recombinant fusion proteins that retained the immunogenicity and antigenicity of their individual components. The fusion proteins induced both T cell and B cell responses, as measured by T cell proliferation, cytokine production, and antibody production. Furthermore, a fusion protein was used as an immunogen with adjuvants in vivo to elicit both cell-mediated and humoral immunity to *M. tuberculosis*. Additionally, a fusion protein of two antigens was made by a fusion construct and used in a vaccine formulation with an adjuvant to afford long-term protection in animals against the development of tuberculosis. The fusion protein was a more effective immunogen than a mixture of the two proteins.

In a specific embodiment of the invention, the isolated or purified *M. tuberculosis* polypeptides of the invention may be formulated as pharmaceutical compositions for administration into a subject in the prevention and/or treatment of *M. tuberculosis* infection. The immunogenicity of the fusion protein may be enhanced by the inclusion of an adjuvant.

In another aspect of the invention, the isolated or purified polynucleotides are used to produce recombinant fusion polypeptide antigens in vitro. Alternatively, the polynucleotides may be administered directly into a subject as DNA vaccines to cause antigen expression in the subject, and the subsequent induction of an anti-*M. tuberculosis* immune response.

4. BRIEF DESCRIPTION OF THE DRAWINGS

Figure 1A:
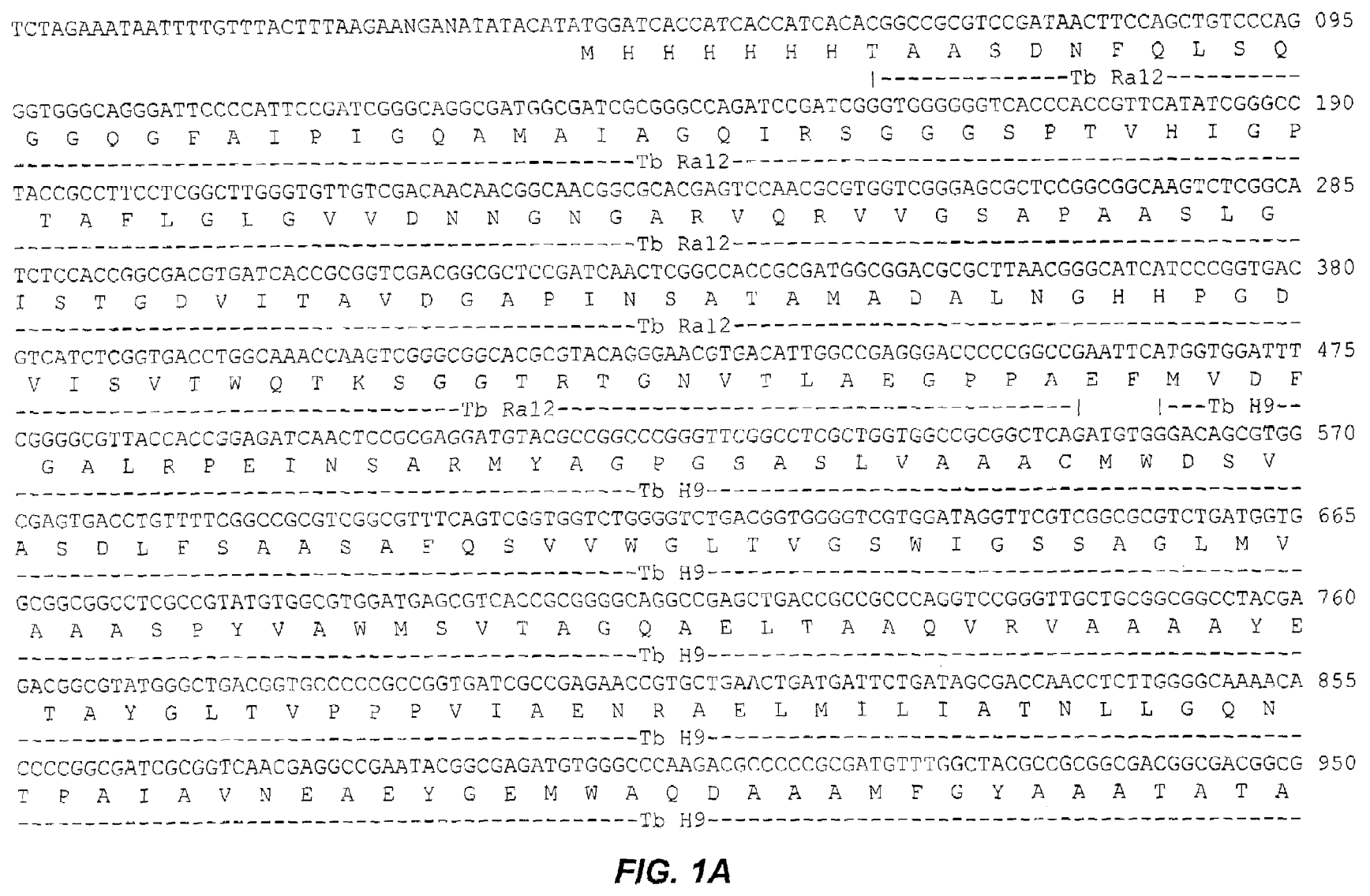
Figure 1B:
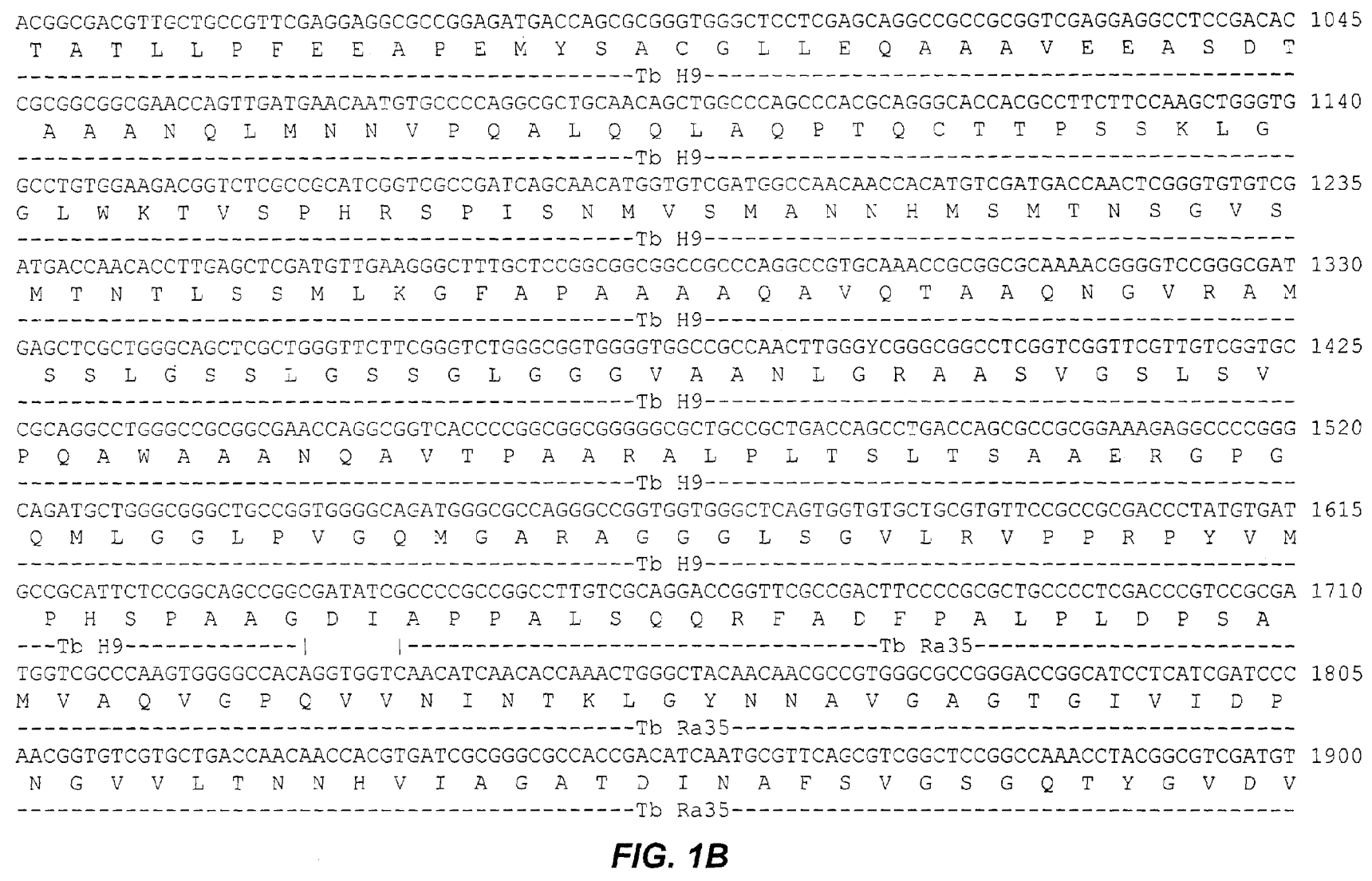

FIGS. 1A and 1B. The nucleotide sequence (SEQ ID NO:1) and amino acid sequence (SEQ ID NO:2) of tri-fusion protein Ra12-TbH9-Ra35.

FIGS. 2A and 2B: The nucleotide sequence (SEQ ID NO:3) and amino acid sequence (SEQ ID NO:4) of tri-fusion protein Erd14-DPV-MT1.

FIG. 3A–3F: T cell proliferation responses of six PPD+ subjects when stimulated with two fusion proteins and their individual components.

FIG. 4A–4F: IFN-γ production of six PPD+ subjects when stimulated with two fusion proteins and their individual components.

FIG. 5A–5F: T cell proliferation of mice immunized with a fusion protein or its individual components and an adjuvant.

Figure 6:
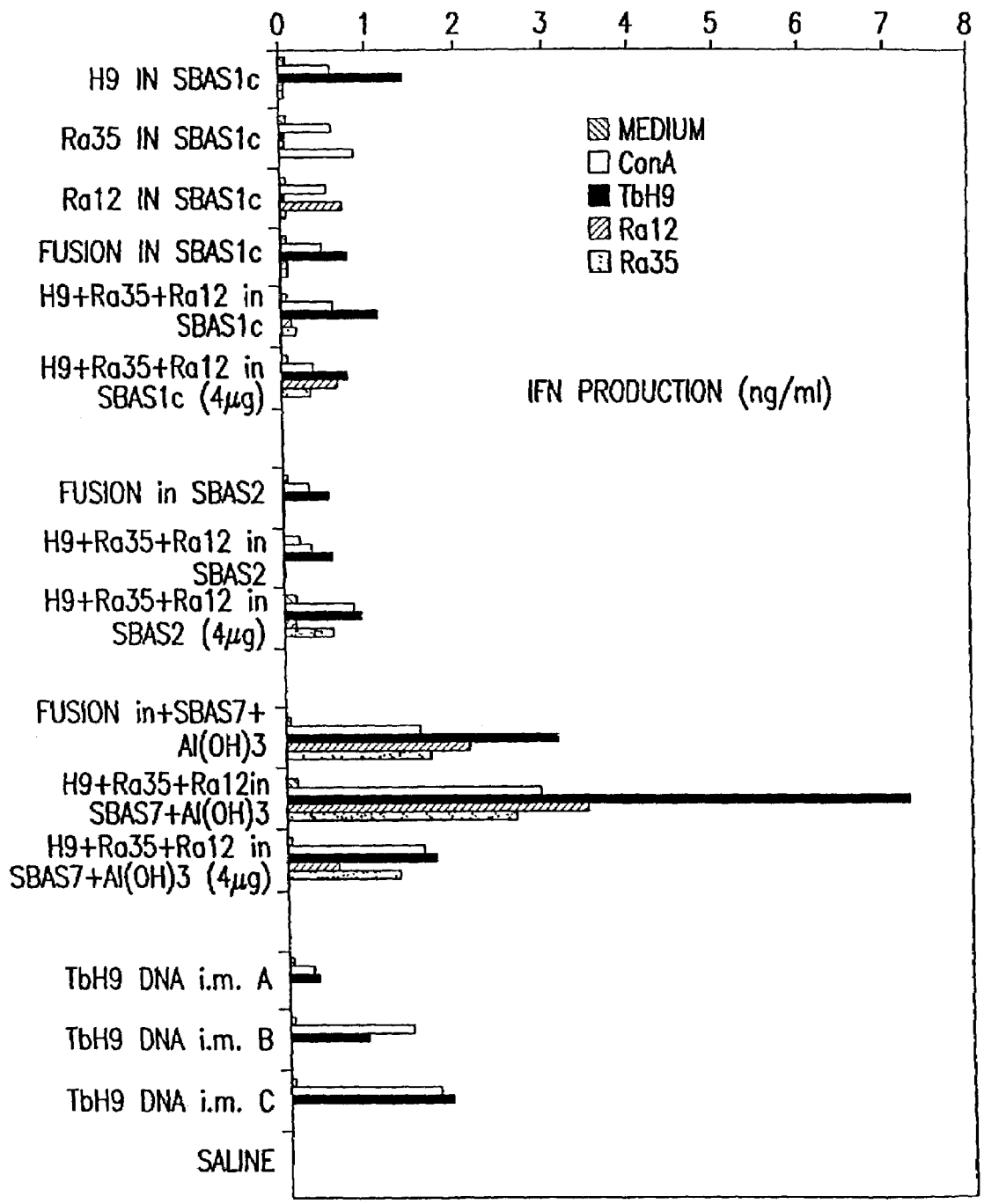

FIG. 6: IFN-γ production of mice immunized with a fusion protein or its individual components and an adjuvant.

Figure 7:
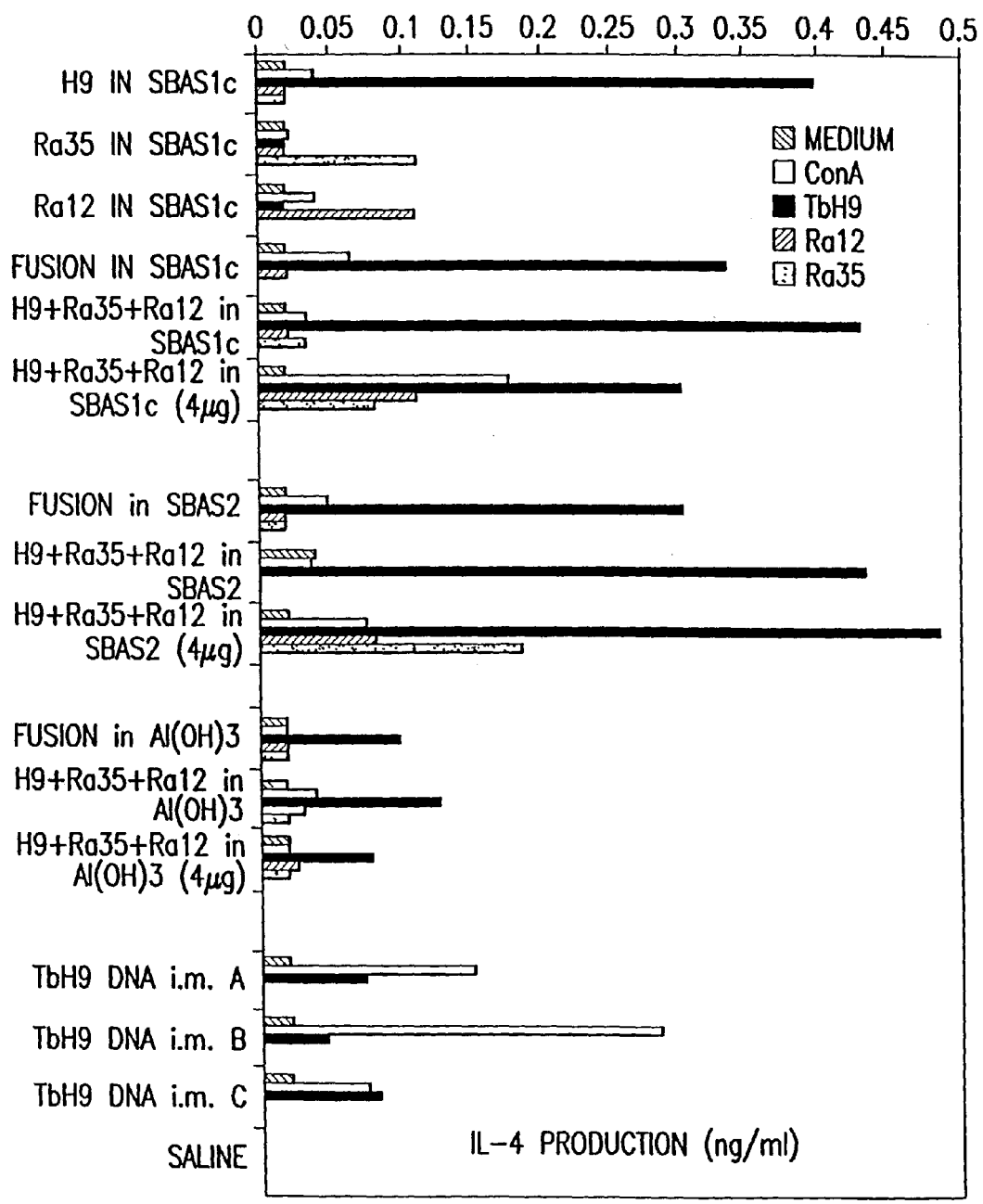
Figure 8A:
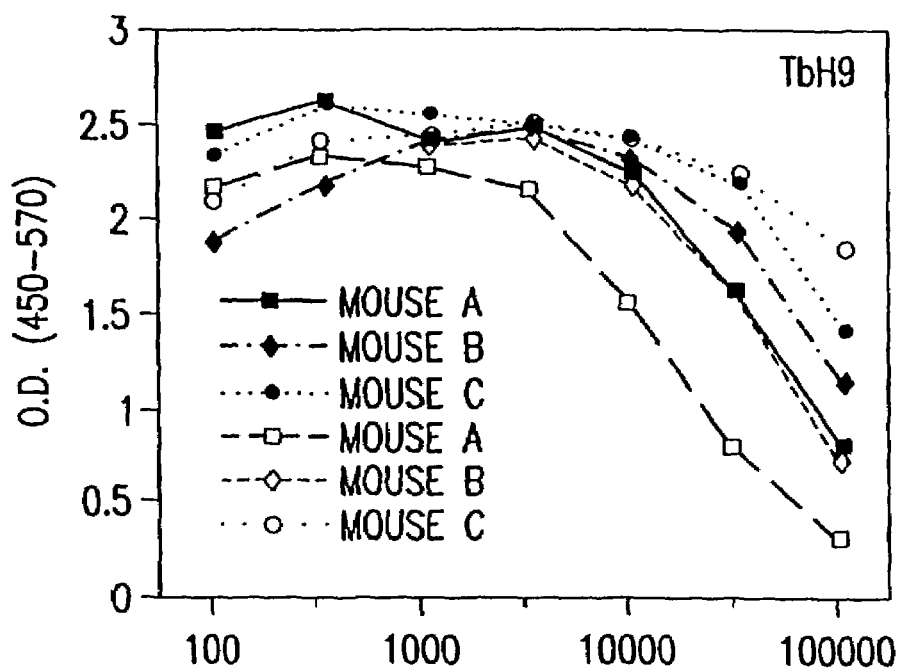
Figure 8B:
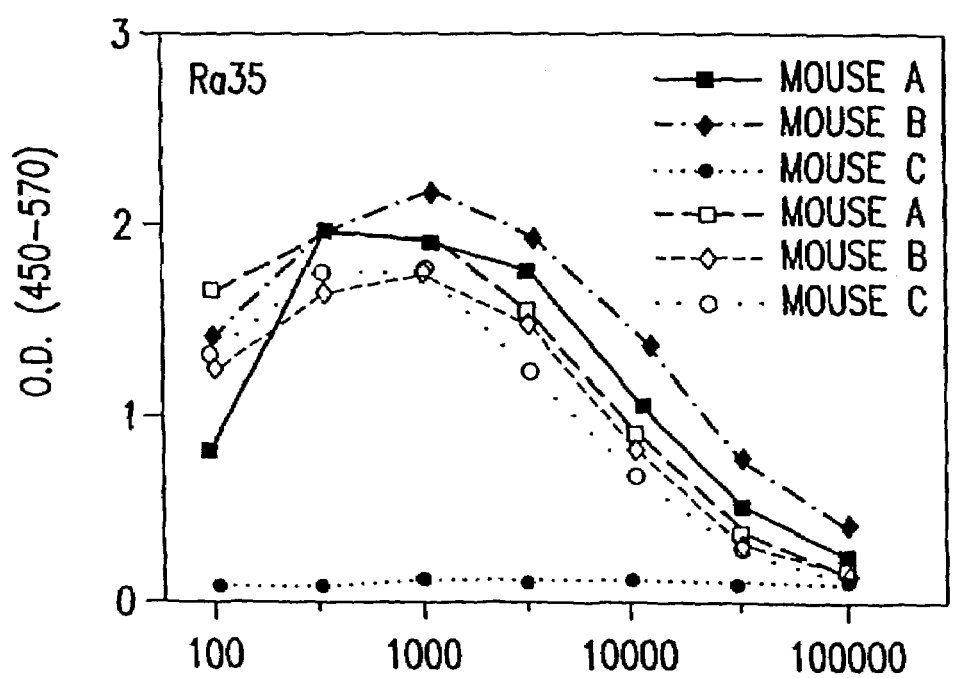
Figure 8C:
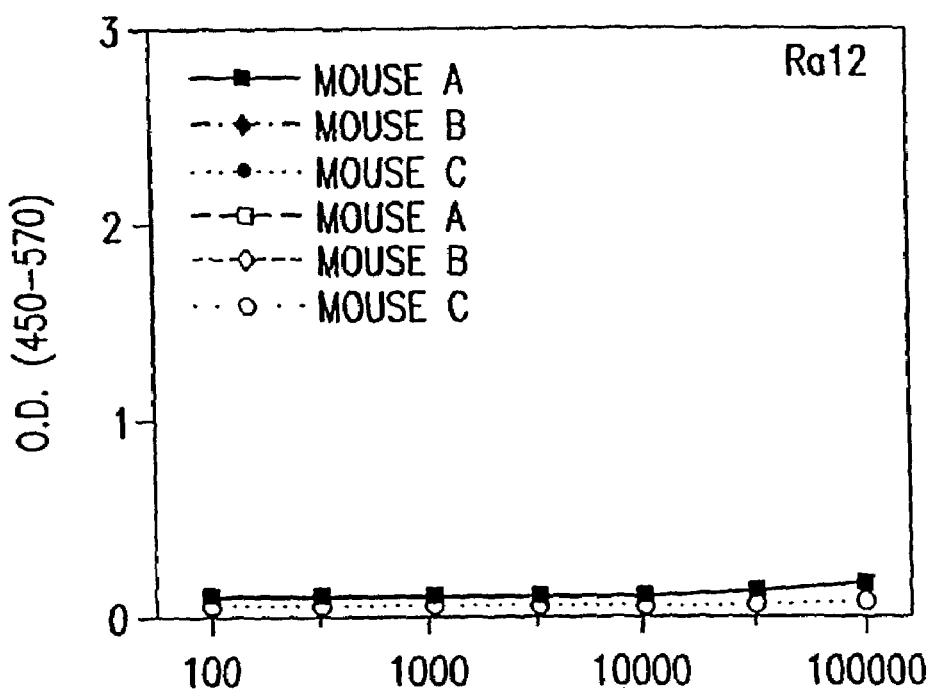
Figure 8D:
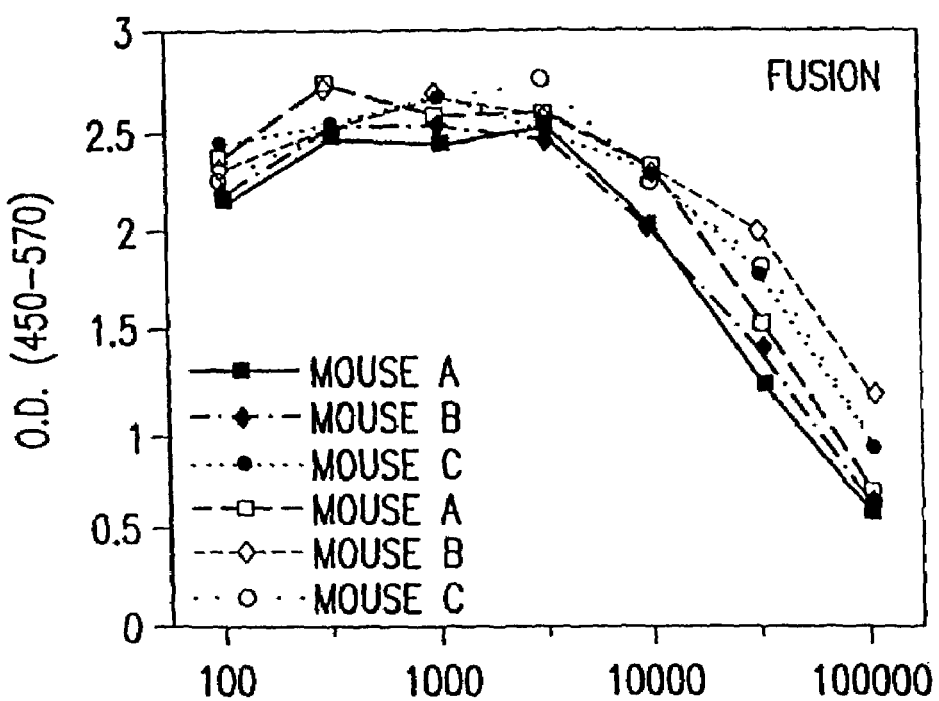
Figure 8E:
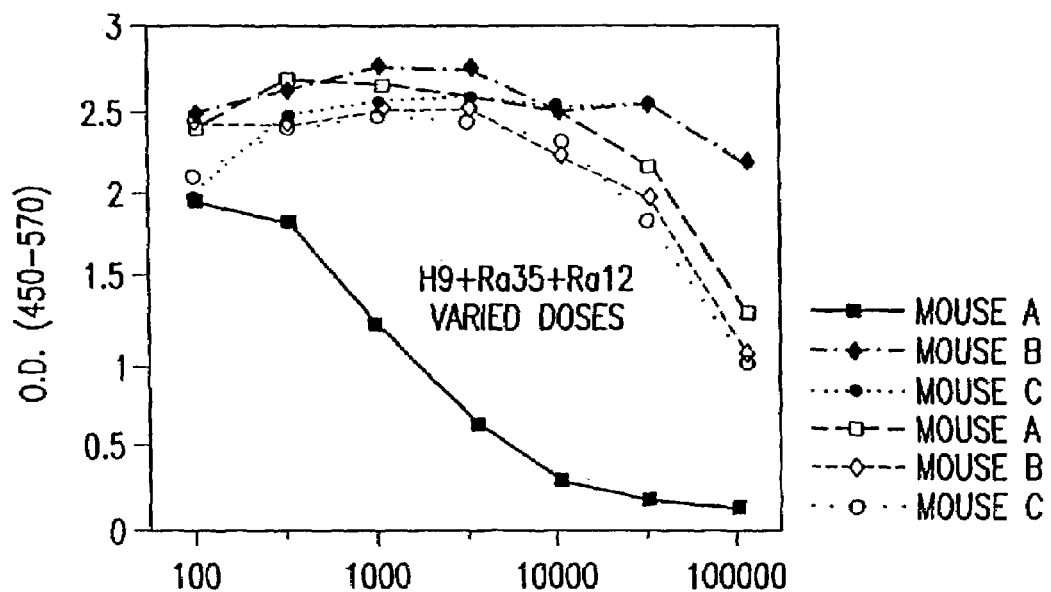
Figure 8F:
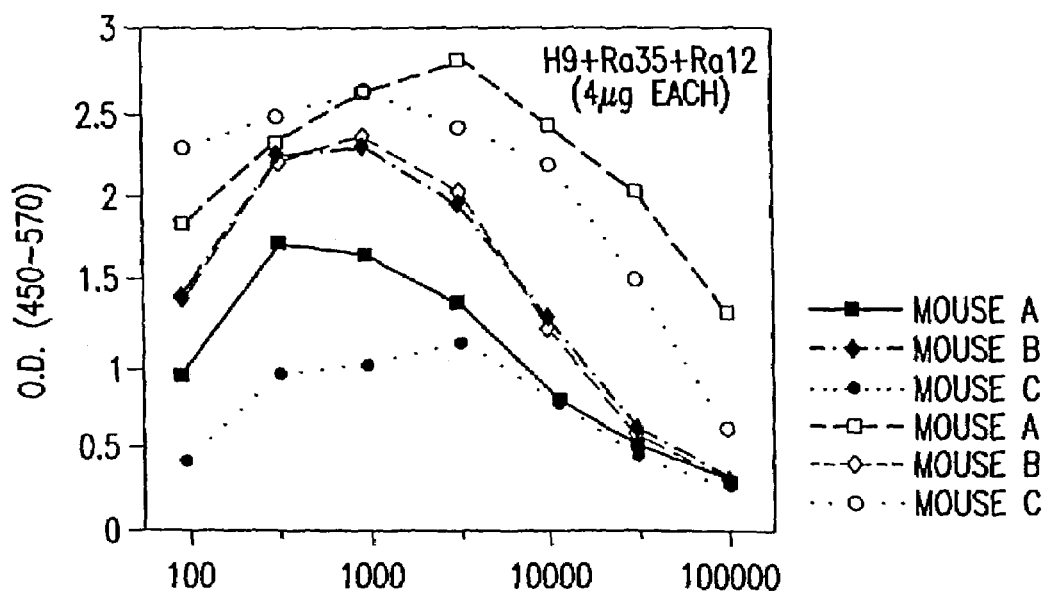

FIG. 7: IL-4 production of mice immunized with a fusion protein or its individual components and an adjuvant.

FIG. 8A–8F: Serum antibody concentrations of mice immunized with a fusion protein or its individual components and an adjuvant.

Figure 9A:
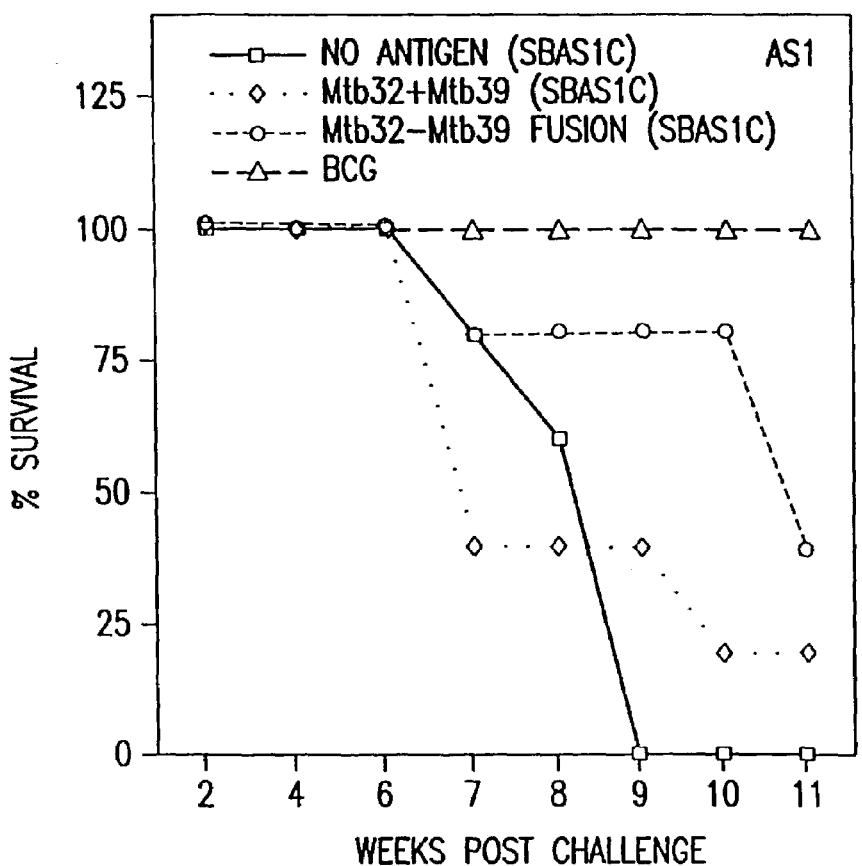
Figure 9B:
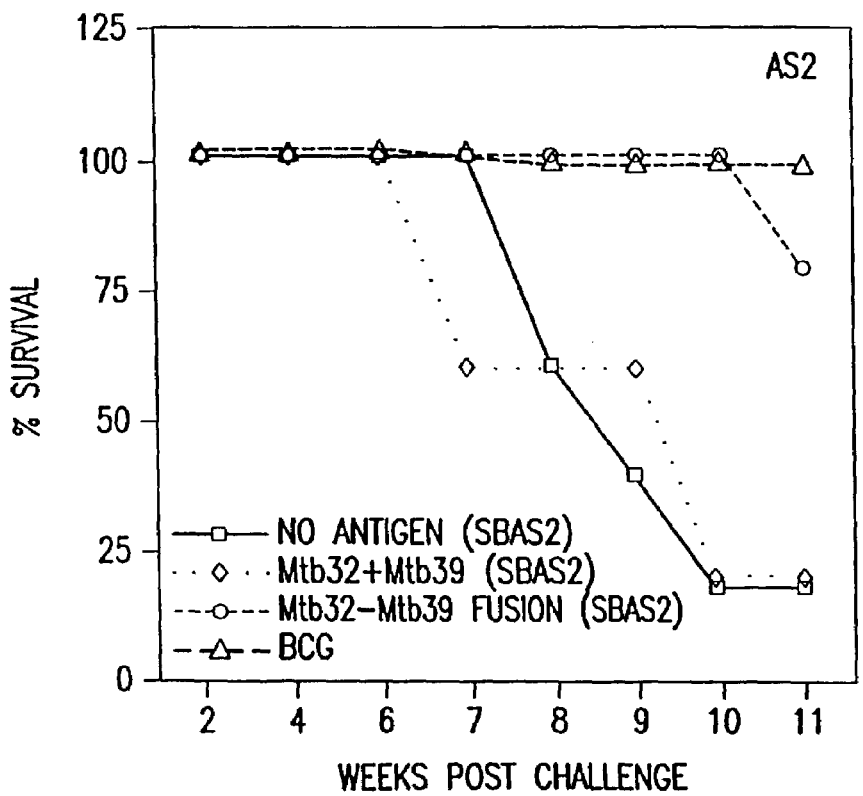
Figure 9C:
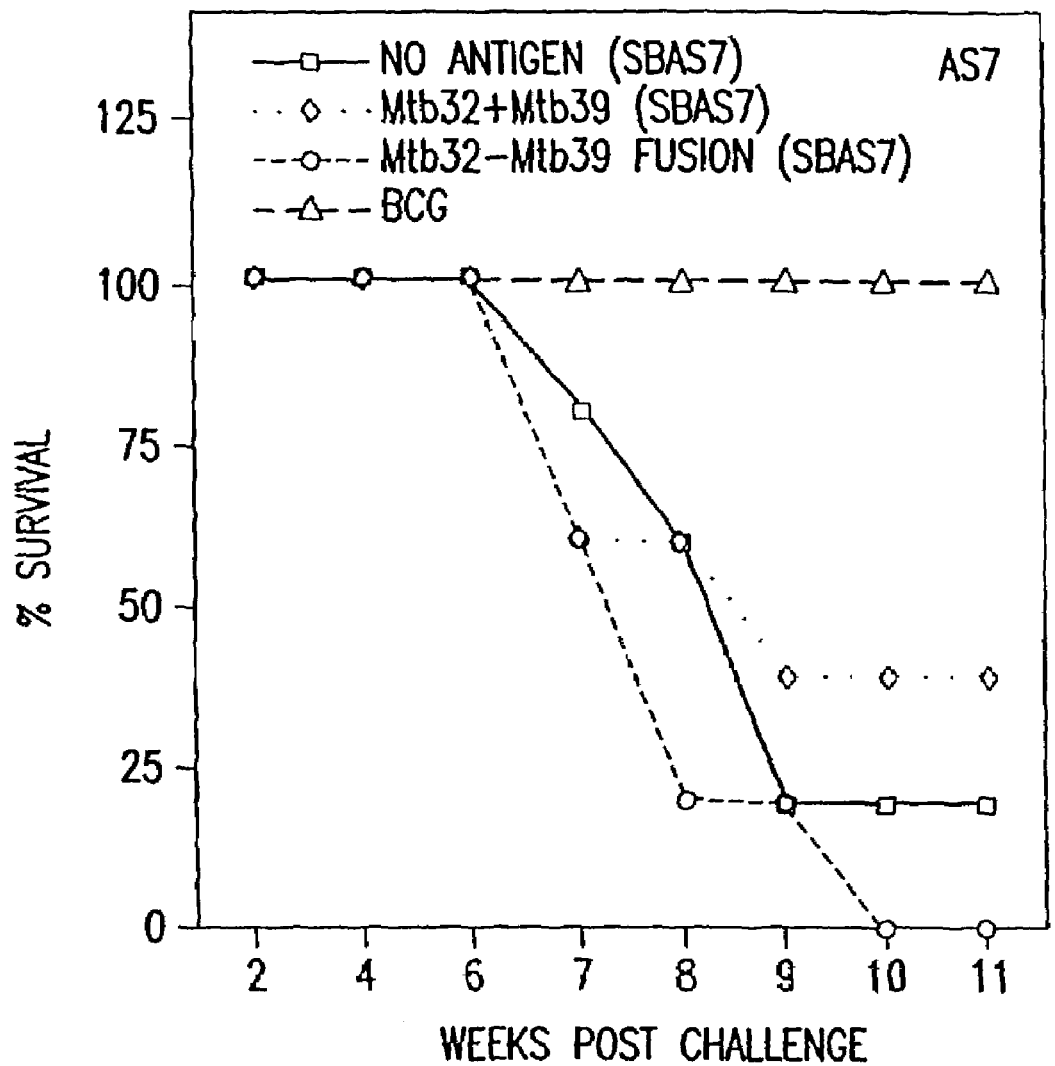

FIG. 9A–9C: Survival of guinea pigs after aerosol challenge of M. tuberculosis. Mtb32A and Mtb39A were formulated in adjuvant SBAS1c (9A), SBAS2 (9B) or SBAS7 (9C), and used as an immunogen in guinea pigs prior to challenge with bacteria. BCG is the positive control.

5. DETAILED DESCRIPTION OF THE INVENTION

5.1. Isolation Of Coding Sequences

The present invention relates to nucleic acid molecules that encode fusion polypeptides of M. tuberculosis. In a specific embodiment by way of example in Section 6, infra, three M. tuberculosis fusion coding sequences were constructed and expressed. In accordance with the invention, any nucleotide sequence which encodes the amino acid sequence of the fusion protein can be used to generate recombinant molecules which direct the expression of the coding sequence.

In order to clone full-length coding sequences or homologous variants to generate the fusion polynucleotides, labeled DNA probes designed from any portion of the nucleotide sequences or their complements disclosed herein may be used to screen a genomic or cDNA library made from various strains of M. tuberculosis to identify the coding sequence of each individual component. Isolation of coding sequences may also be carried out by the polymerase chain reactions (PCR) using two degenerate oligonucleotide primer pools designed on the basis of the coding sequences disclosed herein.

The invention also relates to isolated or purified polynucleotides complementary to the nucleotide sequences of SEQ ID NOS:1 and 3, and polynucleotides that selectively hybridize to such complementary sequences. In a preferred embodiment, a polynucleotide which hybridizes to the sequence of SEQ ID NOS: 1 and 3 or its complementary sequence under conditions of low stringency and encodes a protein that retains the immunogenicity of the fusion proteins of SEQ ID NOS:2 and 4 is provided. By way of example and not limitation, exemplary conditions of low stringency are as follows (see also Shilo and Weinberg, 1981, Proc. Natl. Acad. Sci. USA 78:6789–6792): Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5–20×10⁶ cpm ³²P-labeled probe is used. Filters are incubated in hybridization mixture for 18–20 h at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65–68° C. and re-exposed to film. Other conditions of low stringency which may be used are well known in the art (e.g., as employed for cross-species hybridizations).

In another preferred embodiment, a polynucleotide which hybridizes to the coding sequence of SEQ ID NOS:1 and 3 or its complementary sequence under conditions of high stringency and encodes a protein that retains the immunogenicity of the fusion proteins of SEQ ID NOS:2 and 4 is provided. By way of example and not limitation, exemplary conditions of high stringency are as follows: Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C. in prehybridization mixture containing 100 µg/ml denatured salmon sperm DNA and 5–20×10⁶ cpm of ³²P-labeled probe. Washing of filters is done at 37° C. for 1 h in a solution containing 2×SSC, 0.01% PVP, 0.01% Ficoll, and 0.01% BSA. This is followed by a wash in 0.1×SSC at 50° C. for 45 min before autoradiography. Other conditions of high stringency which may be used are well known in the art.

In yet another preferred embodiment, a polynucleotide which hybridizes to the coding sequence of SEQ ID NOS:1 and 3 or its complementary sequence under conditions of moderate stringency and encodes a protein that retains the immunogenicity of the fusion proteins of SEQ ID NOS:2 and 4 is provided. Exemplary conditions of moderate stringency are as follows: Filters containing DNA are pretreated for 6 h at 55° C. in a solution containing 6×SSC, 5× Denhart's solution, 0.5% SDS and 100 µg/ml denatured salmon sperm DNA. Hybridizations are carried out in the same solution and 5–20×10⁶ cpm ³²P-labeled probe is used. Filters are incubated in hybridization mixture for 18–20 h at 55° C., and then washed twice for 30 minutes at 60° C. in a solution containing 1×SSC and 0.1% SDS. Filters are blotted dry and exposed for autoradiography. Other conditions of moderate stringency which may be used are well-known in the art. Washing of filters is done at 37° C. for 1 h in a solution containing 2×SSC, 0.1% SDS.

5.2. Polypeptides Encoded by the Coding Sequences

In accordance with the invention, a polynucleotide of the invention which encodes a fusion protein, fragments thereof, or functional equivalents thereof may be used to generate recombinant nucleic acid molecules that direct the expression of the fusion protein, fragments thereof, or functional equivalents thereof, in appropriate host cells. The fusion polypeptide products encoded by such polynucleotides may be naturally occurring or altered by molecular manipulation of the coding sequence.

Due to the inherent degeneracy of the genetic code, other DNA sequences which encode substantially the same or a functionally equivalent amino acid sequence, may be used in the practice of the invention for the expression of the fusion polypeptides. Such DNA sequences include those which are capable of hybridizing to the coding sequences or their complements disclosed herein under low, moderate or high stringency conditions described in Sections 5.1, supra.

Altered nucleotide sequences which may be used in accordance with the invention include deletions, additions or substitutions of different nucleotide residues resulting in a sequence that encodes the same or a functionally equivalent gene product. The gene product itself may contain deletions, additions or substitutions of amino acid residues, which result in a silent change thus producing a functionally equivalent antigenic epitope. Such conservative amino acid substitutions may be made on the basis of similarity in polarity, charge, solubility, hydrophobicity, hydrophilicity, and/or the amphipathic nature of the residues involved. For example, negatively charged amino acids include aspartic acid and glutamic acid; positively charged amino acids include lysine, histidine and arginine; amino acids with uncharged polar head groups having similar hydrophilicity values include the following: glycine, asparagine, glutamine, serine, threonine and tyrosine; and amino acids with nonpolar head groups include alanine, valine, isoleucine, leucine, phenylalanine, proline, methionine and tryptophan.

The nucleotide sequences of the invention may be engineered in order to alter the fusion protein coding sequence for a variety of ends, including but not limited to, alterations which modify processing and expression of the gene product. For example, mutations may be introduced using techniques which are well known in the art, e.g., site-directed mutagenesis, to insert new restriction sites, to alter glycosylation patterns, phosphorylation, etc.

In an alternate embodiment of the invention, the coding sequence of a fusion protein could be synthesized in whole or in part, using chemical methods well known in the art See, e.g., Caruthers et al., 1980, Nuc. Acids Res. Symp. Ser. 7:215–233; Crea and Horn, 180, Nuc. Acids Res. 9(10): 2331; Matteucci and Caruthers, 1980, Tetrahedron Letter 21:719; and Chow and Kempe, 1981, Nuc. Acids Res. 9(12):2807–2817. Alternatively, the polypeptide itself could be produced using chemical methods to synthesize an amino acid sequence in whole or in part. For example, peptides can be synthesized by solid phase techniques, cleaved from the resin, and purified by preparative high performance liquid chromatography. (See Creighton, 1983, *Proteins Structures And Molecular Principles*, W.H. Freeman and Co., N.Y. pp. 50–60). The composition of the synthetic polypeptides may be confirmed by amino acid analysis or sequencing (e.g., the Edman degradation procedure; see Creighton, 1983, *Proteins, Structures and Molecular Principles*, W.H. Freeman and Co., N.Y., pp. 34–49).

Additionally, the coding sequence of a fusion protein can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, chemical mutagenesis, in vitro site-directed mutagenesis (Hutchinson, C., et al., 1978, J. Biol. Chem 253:6551), use of TAB® linkers (Pharmacia), and the like. It is important that the manipulations do not destroy immunogenicity of the fusion polypeptides.

In addition, nonclassical amino acids or chemical amino acid analogs can be introduced as a substitution or addition into the sequence. Non-classical amino acids include, but are not limited to, the D-isomers of the common amino acids, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general. Furthermore, the amino acid can be D (dextrorotary) or L (levorotary).

In a specific embodiment, the coding sequences of each antigen in the fusion protein are joined at their amino- or carboxy-terminus via a peptide bond in any order. Alternatively, the antigens are connected by a flexible polylinker such as Gly-Cys-Gly or Gly-Gly-Gly-Gly-Ser repeated 1 to 3 times (SEQ ID NOS:5–7 and 8–10, respectively) (Bird et al., 1988, Science 242:423–426; Chaudhary et al., 1990, Proc. Nat'l. Acad. Sci. U.S.A. 87:1066–1070). In one embodiment, such a protein is produced by recombinant expression of a nucleic acid encoding the protein. Such a fusion product can be made by ligating the appropriate nucleic acid sequences encoding the desired amino acid sequences to each other by methods known in the art, in the proper coding frame, and expressing the product by methods commonly known in the art. Alternatively, such a product may be made by protein synthetic techniques, e.g., by use of a peptide synthesizer. Coding sequences for other molecules such as a cytokine or an adjuvant can be added to the fusion polynucleotide as well.

5.3. Production of Fusion Proteins

In order to produce a *M. tuberculosis* fusion protein of the invention, the nucleotide sequence coding for the protein, or a functional equivalent, is inserted into an appropriate expression vector, i.e., a vector which contains the necessary elements for the transcription and translation of the inserted coding sequence. The host cells or cell lines transfected or transformed with recombinant expression vectors can be used for a variety of purposes. These include, but are not limited to, large scale production of the fusion protein.

Methods which are well known to those skilled in the art can be used to construct expression vectors containing a fusion coding sequence and appropriate transcriptional/ translational control signals. These methods include in vitro recombinant DNA techniques, synthetic techniques and in vivo recombination/genetic recombination. (See, e.g., the techniques described in Sambrook et al., 1989, Molecular Cloning A Laboratory Manual, Cold Spring Harbor Laboratory, N.Y. and Ausubel et al., 1989, Current Protocols in Molecular Biology, Greene Publishing Associates and Wiley Interscience, N.Y.). RNA capable of encoding a polypeptide may also be chemically synthesized (Gait, ed., 1984, Oligonucleoide Synthesis, IRL Press, Oxford).

5.3.1. Expression Systems

A variety of host-expression vector systems may be utilized to express a fusion protein coding sequence. These include, but are not limited to, microorganisms such as bacteria (e.g. *E. coli, B. subtilis*) transformed with recombinant bacteriophage DNA, plasmid DNA or cosmid DNA expression vectors containing a coding sequence; yeast (e.g. *Saccharomycdes, Pichia*) transformed with recombinant yeast expression vectors containing a coding sequence; insect cell systems infected with recombinant virus expression vectors (e.g., baculovirus) containing a coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing a coding sequence; or mammalian cell systems (e.g. COS, CHO, BHK, 293, 3T3 cells). The expression elements of these systems vary in their strength and specificities.

Depending on the host/vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter; cytomegalovirus promoter) and the like may be used; when cloning in insect cell systems, promoters such as the baculovirus polyhedron promoter may be used; when cloning in plant cell systems, promoters derived from the genome of plant cells (e.g., heat shock promoters; the promoter for the small subunit of RUBISCO; the promoter for the chlorophyll α/β binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5K promoter) may be used; when generating cell lines that contain multiple copies of a the antigen coding sequence, SV40-, BPV- and EBV-based vectors may be used with an appropriate selectable marker.

Bacterial systems are preferred for the expression of $M.$ $tuberculosis$ antigens. For in vivo delivery, a bacterium such as $Bacillus$-Calmette-Guerrin may be engineered to express a fusion polypeptide of the invention on its cell surface. A number of other bacterial expression vectors may be advantageously selected depending upon the use intended for the expressed products. For example, when large quantities of the fusion protein are to be produced for formulation of pharmaceutical compositions, vectors which direct the expression of high levels of fusion protein products that are readily purified may be desirable. Such vectors include, but are not limited to, the $E.$ $coli$ expression vector pUR278 (Ruther et al., 1983, EMBO J. 2:1791), in which a coding sequence may be ligated into the vector in frame with the lacZ coding region so that a hybrid protein is produced; pIN vectors (Inouye & Inouye, 1985, Nucleic acids Res. 13:3101–3109; Van Heeke & Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can be purified easily from lysed cells by adsorption to glutathione-agarose beads followed by elution in the presence of free glutathione. The pGEX vectors are designed to include thrombin or factor Xa protease cleavage sites so that the cloned fusion polypeptide of interest can be released from the GST moiety.

5.3.2. Protein Purification

Once a recombinant protein is expressed, it can be identified by assays based on the physical or functional properties of the product, including radioactive labeling of the product followed by analysis by gel electrophoresis, radioimmunoassay, ELISA, bioassays, etc.

Once the encoded protein is identified, it may be isolated and purified by standard methods including chromatography (e.g., high performance liquid chromatography, ion exchange, affinity, and sizing column chromatography), centrifugation, differential solubility, or by any other standard technique for the purification of proteins. The actual conditions used will depend, in part, on factors such as net charge, hydrophobicity, hydrophilicity, etc., and will be apparent to those having skill in the art. The functional properties may be evaluated using any suitable assay such as antibody binding, induction of T cell proliferation, stimulation of cytokine production such as IL2, IL-4 and IFN-γ. For the practice of the present invention, it is preferred that each fusion protein is at least 80% purified from other proteins. It is more preferred that they are at least 90% purified. For in vivo administration, it is preferred that the proteins are greater than 95% purified.

5.4. Uses of the Fusion Protein Coding Sequence

The fusion protein coding sequence of the invention may be used to encode a protein product for use as an immunogen to induce and/or enhance immune responses to $M.$ $tuberculosis$. In addition, such coding sequence may be ligated with a coding sequence of another molecule such as cytokine or an adjuvant. Such polynucleotides may be used in vivo as a DNA vaccine (U.S. Pat. Nos. 5,589,466; 5,679,647; 5,703,055). In this embodiment of the invention, the polynucleotide expresses its encoded protein in a recipient to directly induce an immune response. The polynucleotide may be injected into a naive subject to prime an immune response to its encoded product, or administered to an infected or immunized subject to enhance the secondary immune responses.

In a preferred embodiment, a therapeutic composition comprises a fusion protein coding sequence or fragments thereof that is part of an expression vector. In particular, such a polynucleotide contains a promoter operably linked to the coding region, said promoter being inducible or constitutive, and, optionally, tissue-specific. In another embodiment, a polynucleotide contains a coding sequence flanked by regions that promote homologous recombination at a desired site in the genome, thus providing for intrachromosomal expression of the coding sequence (Koller and Smithies, 1989, Proc. Natl. Acad. Sci. USA 86:8932–8935; Zijlstra et al., 1989, Nature 342:435–438).

Delivery of the nucleic acid into a subject may be either direct, in which case the subject is directly exposed to the nucleic acid or nucleic acid-carrying vector, or indirect, in which case, cells are first transformed with the nucleic acid in vitro, then transplanted into the subject. These two approaches are known, respectively, as in vivo or ex vivo gene transfer.

In a specific embodiment, the nucleic acid is directly administered in vivo, where it is expressed to produce the encoded fusion protein product. This can be accomplished by any of numerous methods known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering it in linkage to a peptide which is known to enter the nucleus, by administering it in linkage to a ligand subject to receptor-mediated endocytosis (see e.g., Wu and Wu, 1987, J. Biol. Chem. 262:4429–4432) which can be used to target cell types specifically expressing the receptors, etc. In another embodiment, a nucleic acid-ligand complex can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992; WO 92/22635 dated Dec. 23, 1992; WO092/20316 dated Nov. 26, 1992; WO093/14188 dated Jul. 22, 1993; WO 93/20221 dated Oct. 14, 1993). Alternatively, the nucleic acid can be introduced intracellularly and incorporated within host cell DNA for expression, by homologous recombination (Koller and Smithies, 1989, Proc. Natl. Acad. Sci. USA 86:8932–8935; Zijlstra et al., 1989, Nature 342: 435–438).

In a specific embodiment, a viral vector such as a retroviral vector can be used (see Miller et al., 1993, Meth. Enzymol. 217:581–599). Retroviral vectors have been modified to delete retroviral sequences that are not necessary for packaging of the viral genome and integration into host cell DNA. A fusion coding sequence is cloned into the vector, which facilitates delivery of the nucleic acid into a recipient. More detail about retroviral vectors can be found in Boesen et al., 1994, Biotherapy 6:291–302, which describes the use of a retroviral vector to deliver the mdrI gene to hematopoietic stem cells in order to make the stem cells more resistant to chemotherapy. Other references illustrating the use of retroviral vectors in gene therapy are: Clowes et al., 1994, J. Clin. Invest. 93:644–651; Kiem et al., 1994, Blood 83:1467–1473; Salmons and Gunzberg, 1993, Human Gene Therapy 4:129–141; and Grossman and Wilson, 1993, Curr. Opin. in Genetics and Devel. 3:110–114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Adeno-associated virus (AAV) has also been proposed for use in in vivo gene transfer (Walsh et al., 1993, Proc. Soc. Exp. Biol. Med. 204:289–300.

Another approach involves transferring a construct to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a subject.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see e.g., Loeffler and Behr, 1993, Meth. Enzymol. 217:599–618; Cohen et al., 1993, Meth. Enzymol. 217:618–644; Cline, 1985, Pharmac. Ther. 29:69–92) and may be used in accordance with the present invention.

5.5. Uses of the Fusion Protein

Purified or partially purified fusion proteins or fragments thereof may be formulated as a vaccine or therapeutic composition. Such composition may include adjuvants to enhance immune responses. Commonly used adjuvants include, but are not limited to, aluminum hydroxide, mineral oil, lipid A and *B. pertussis*. In addition, such proteins may be further suspended in an oil emulsion to cause a slower release of the proteins in vivo upon injection. The optimal ratios of each component in the formulation may be determined by techniques well known to those skilled in the art.

Such a formulation may be administered to a subject per se or in the form of a pharmaceutical or therapeutic composition. Pharmaceutical compositions comprising the proteins may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the polypeptides into preparations which can be used pharmaceutically. Proper formulation is dependent upon the route of administration chosen.

For topical administration, the proteins may be formulated as solutions, gels, ointments, creams, suspensions, etc. as are well-known in the art.

Systemic formulations include those designed for administration by injection, e.g. subcutaneous, intravenous, intramuscular, intrathecal or intraperitoneal injection, as well as those designed for transdermal, transmucosal, oral or pulmonary administration.

For injection, the proteins may be formulated in aqueous solutions, preferably in physiologically compatible buffers such as Hanks's solution, Ringer's solution, or physiological saline buffer. The solution may contain formulatory agents such as suspending, stabilizing and/or dispersing agents. Alternatively, the proteins may be in powder form for constitution with a suitable vehicle, e.g., sterile pyrogen-free water, before use.

For transmucosal administration, penetrants appropriate to the barrier to be permeated are used in the formulation. Such penetrants are generally known in the art.

For oral administration, a composition can be readily formulated by combining the proteins with pharmaceutically acceptable carriers well known in the art. Such carriers enable the proteins to be formulated as tablets, pills, dragees, capsules, liquids, gels, syrups, slurries, suspensions and the like, for oral ingestion by a subject to be treated. For oral solid formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate.

If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. Additionally, flavoring agents, preservatives, coloring agents and the like may be added.

For buccal administration, the proteins may take the form of tablets, lozenges, etc. formulated in conventional manner.

For administration by inhalation, the proteins for use according to the present invention are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the proteins and a suitable powder base such as lactose or starch.

The proteins may also be formulated in rectal or vaginal compositions such as suppositories or retention enemas, e.g, containing conventional suppository bases such as cocoa butter or other glycerides.

In addition to the formulations described previously, the proteins may also be formulated as a depot preparation. Such long acting formulations may be administered by implantation (for example subcutaneously or intramuscularly) or by intramuscular injection. Thus, for example, the proteins may be formulated with suitable polymeric or hydrophobic materials (for example as an emulsion in an acceptable oil) or ion exchange resins, or as sparingly soluble derivatives, for example, as a sparingly soluble salt.

Alternatively, other pharmaceutical delivery systems may be employed. Liposomes and emulsions are well known examples of delivery vehicles that may be used to deliver an antigen. Certain organic solvents such as dimethylsulfoxide also may be employed, although usually at the cost of greater toxicity. Additionally, the proteins may be delivered using a sustained-release system, such as semipermeable matrices of solid polymers containing the therapeutic or vaccinating agent. Various sustained-release materials have been established and are well known by those skilled in the art. Sustained-release capsules may, depending on their chemical nature, release the proteins for a few weeks up to over 100 days. Depending on the chemical nature and the biological stability of the reagent, additional strategies for protein stabilization may be employed.

Determination of an effective amount of the fusion protein for inducing an immune response in a subject is well within the capabilities of those skilled in the art, especially in light of the detailed disclosure provided herein.

An effective dose can be estimated initially from in vitro assays. For example, a dose can be formulated in animal models to achieve an induction of an immune response using techniques that are well known in the art. One having ordinary skill in the art could readily optimize administration to humans based on animal data. Dosage amount and interval may be adjusted individually. For example, when used as a vaccine, the polypeptides and/or polynucleotides of the invention may be administered in about 1 to 3 doses for a 1–36 week period. Preferably, 3 doses are administered, at intervals of about 3–4 months, and booster vaccinations may be given periodically thereafter. Alternate protocols may be appropriate for individual patients. A suitable dose is an amount of polypeptide or DNA that, when administered as described above, is capable of raising an immune response in an immunized patient sufficient to protect the patient from M. tuberculosis infection for at least 1–2 years. In general, the amount of polypeptide present in a dose (or produced in situ by the DNA in a dose) ranges from about 1 pg to about 100 mg per kg of host, typically from about 10 pg to about 1 mg, and preferably from about 100 pg to about 1 μg. Suitable dose range will vary with the size of the patient, but will typically range from about 0.1 mL to about 5 mL.

The invention having been described, the following examples are offered by way of illustration and not limitation.

6. EXAMPLE

Fusion Proteins of *M. tuberculosis* Antigens Retain Immunogenicity of the Individual Components

6.1. Materials and Methods

6.1.1. Construction of Fusion Proteins

Coding sequences were modified by PCR and cloned into an expression plasmid. Each plasmid contained three coding sequences ligated end to end. The fusion polynucleotide was inserted into vector pET-12b. Three coding sequences for antigens Ra12, TbH9 and Ra35 were ligated to encode one fusion protein (SEQ ID NOS: 1 and 2). Another three coding sequences for antigens Erd14, DPV and MT1 were ligated to encode a second fusion protein (SEQ ID NOS: 3 and 4). The recombinant proteins were expressed in *E. coli* with six histidine residues at the amino-terminal portion using the pET plasmid vector (pET-17b) and a T7 RNA polymerase expression system (Novagen, Madison, Wis.). *E. coli* strain BL21 (DE3) pLysE (Novagen) was used for high level expression.

The recombinant (His-Tag) fusion proteins were purified from the soluble supernatant or the insoluble inclusion body of 500 ml of IPTG induced batch cultures by affinity chromatography using the one step QIAexpress Ni-NTA Agarose matrix (QIAGEN, Chatsworth, Calif.) in the presence of 8M urea. Briefly, 20 ml of an overnight saturated culture of BL21 containing the pET construct was added into 500 ml of 2xYT media containing 50 ug/ml ampicillin and 34 ug/ml chloramphenicol, grown at 37° C. with shaking. The bacterial cultures were induced with 2 mM IPTG at an OD 560 of 0.3 and grown for an additional 3 h (OD=1.3 to 1.9). Cells were harvested from 500 ml batch cultures by centrifugation and resuspended in 20 ml of binding buffer (0.1 M sodium phosphate, pH 8.0; 10 mM Tris-HCl, pH 8.0) containing 2 mM PMSF and 20 ug/ml leupeptin plus one Complete protease inhibitor tablet (Boehringer Mannheim) per 25 ml. *E. coli* was lysed by freeze-thaw followed by brief sonication, then spun at 12 k rpm for 30 mm to pellet the inclusion bodies.

The inclusion bodies were washed three times in 1% CHAPS in 10 mM Tris-HCl (pH 8.0). This step greatly reduced the level of contaminating LPS. The inclusion body was finally solubilized in 20 ml of binding buffer containing 8 M urea or 8M urea was added directly into the soluble supernatant. Recombinant fusion proteins with His-Tag residues were batch bound to Ni-NTA agarose resin (5 ml resin per 500 ml inductions) by rocking at room temperature for 1 h and the complex passed over a column. The flow through was passed twice over the same column and the column washed three times with 30 ml each of wash buffer (0.1 M sodium phosphate and 10 mM Tris-HCL, pH 6.3) also containing 8 M urea. Bound protein was eluted with 30 ml of 150 mM immidazole in wash buffer and 5 ml fractions collected. Fractions containing each recombinant fusion protein were pooled, dialyzed against 10 mM TrisHCl (pH 8.0) bound one more time to the Ni-NTA matrix, eluted and dialyzed in 10 mM Tris-HCL (pH 7.8). The yield of recombinant protein varies from 25–150 mg per liter of induced bacterial culture with greater than 98% purity. Recombinant proteins were assayed for endotoxin contamination using the Limulus assay (BioWhittaker) and were shown to contain <10 E.U.Img.

6.1.2. Interferon-γ Assay

Spleens from mice were removed asceptically and single cell suspension prepared in complete RPMI following lysis of red blood cells. 100 ul of cells ($2\times10^{-5}$ cells) were plated per well in a 96-well flat bottom microtiter plate. Cultures were stimulated with the indicated recombinant proteins for 24 h and the supernatant assayed for IFN-γ.

The levels of supernatant IFN-γ was analysed by sandwich ELISA, using antibody pairs and procedures available from PharMingen. Standard curves were generated using recombinant mouse cytokines. ELISA plates (Corning) were coated with 50 μl/well (1 μg/ml, in 0.1 M bicarbonate coating buffer, pH9.6) of a cytokine capture mAb (rat anti-mouse IFN-γ (PharMingen; Cat. # 18181D)), and incubated for 4 hr at room temp. Shake out plate contents and block with PBS-0.05% Tween, 1.0% BSA (200 μ/well) overnight at 4° C. and washed for 6× in PBS-0.1% Tween. Standards (mouse IFN-γ) and supernatant samples diluted in PBS-0.05% Tween, 0.1% BSA were then added for 2 hr at room temp. The plates were washed as above and then incubated for 2 hr at room temperature with 100 ul/well of a second Ab (biotin rat α mouse IFN-γ (Cat. # 18112D; PharMingen) at 0.5 μg/ml diluted in PBS-0.05% Tween, 0.1% BSA. After washing, plates were incubated with 100 μl/well of streptavidin-HRP (Zymed) at a 1:2500 dilution in PBS-0.05% Tween, 0.1% BSA at room temp for 1 hr. The plates were washed one last time and developed with 100 μl/well TMB substrate (3,3',5,5'-tetramethylbenzidine, Kirkegaard and Perry, Gaithersburg, Md.) and the reaction stopped after color develops, with $H_2SO_4$, 50 μl/well. Absorbance (OD) were determined at 450 nm using 570 nm as a reference wavelength and the cytokine concentration evaluated using the standard curve.

6.2. RESULTS

Three coding sequences for *M. tuberculosis* antigens were inserted into an expression vector for the production of a fusion protein. The antigens designated Ra12, TbH9 and Ra35 were produced as one recombinant fusion protein (FIGS. 1A and B). Antigens Erd14, DPV and MTI were produced as a second fusion protein (FIG. 2). The two fusion proteins were affinity purified for use in in vitro and in vivo assays.

Figure 3B:
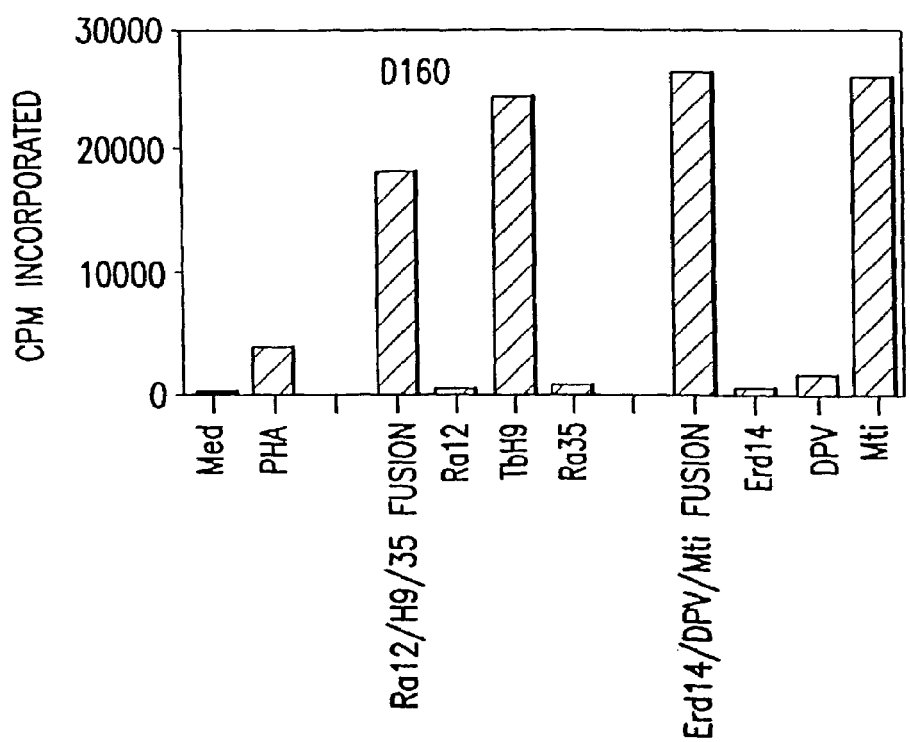
Figure 3C:
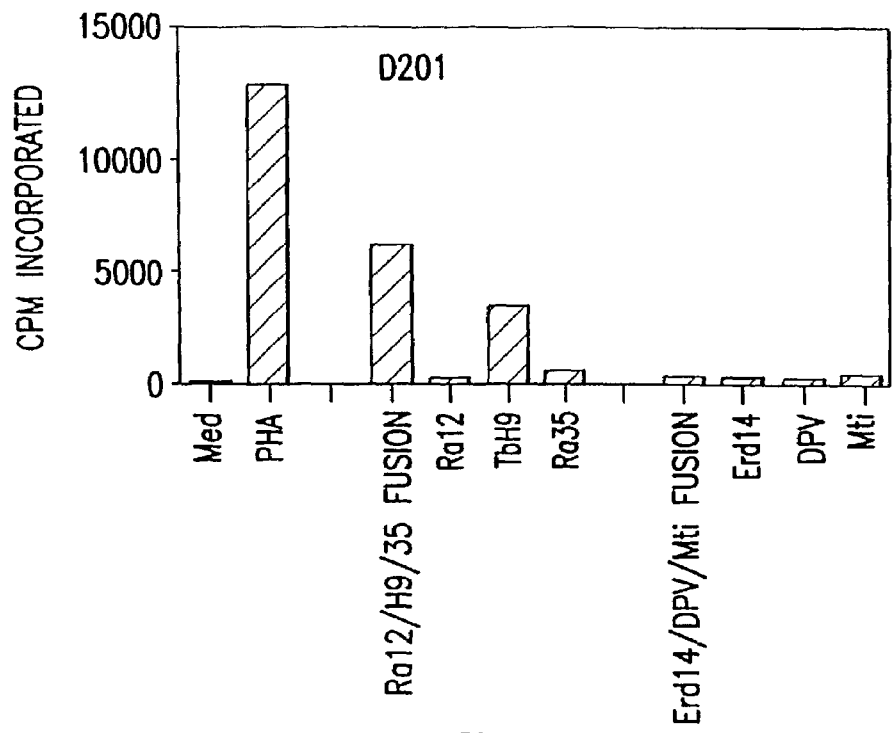
Figure 3D:
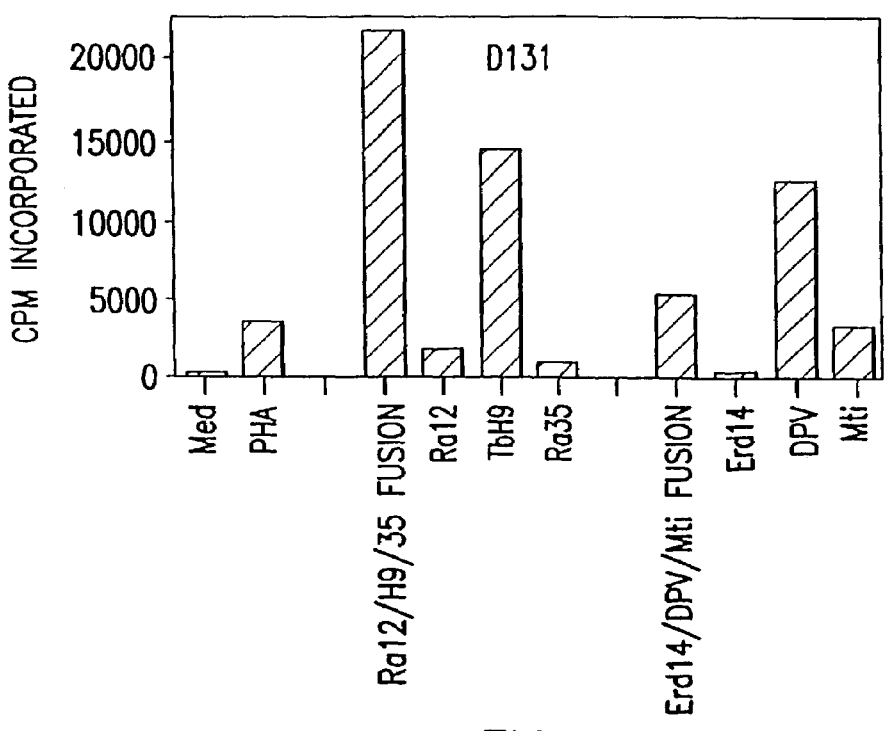
Figure 3E:
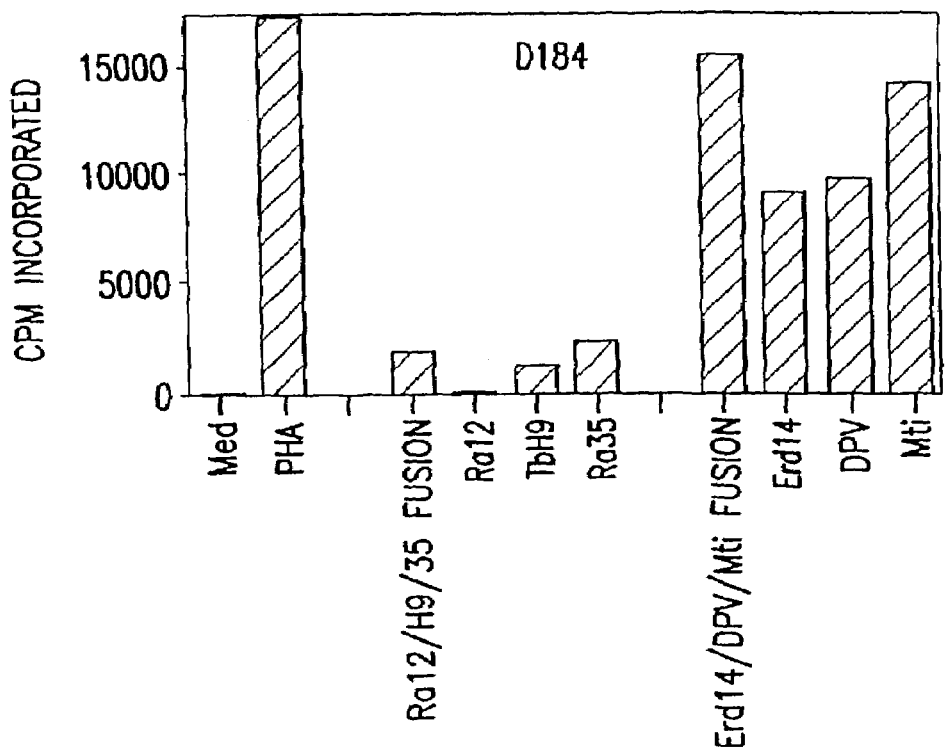
Figure 3F:
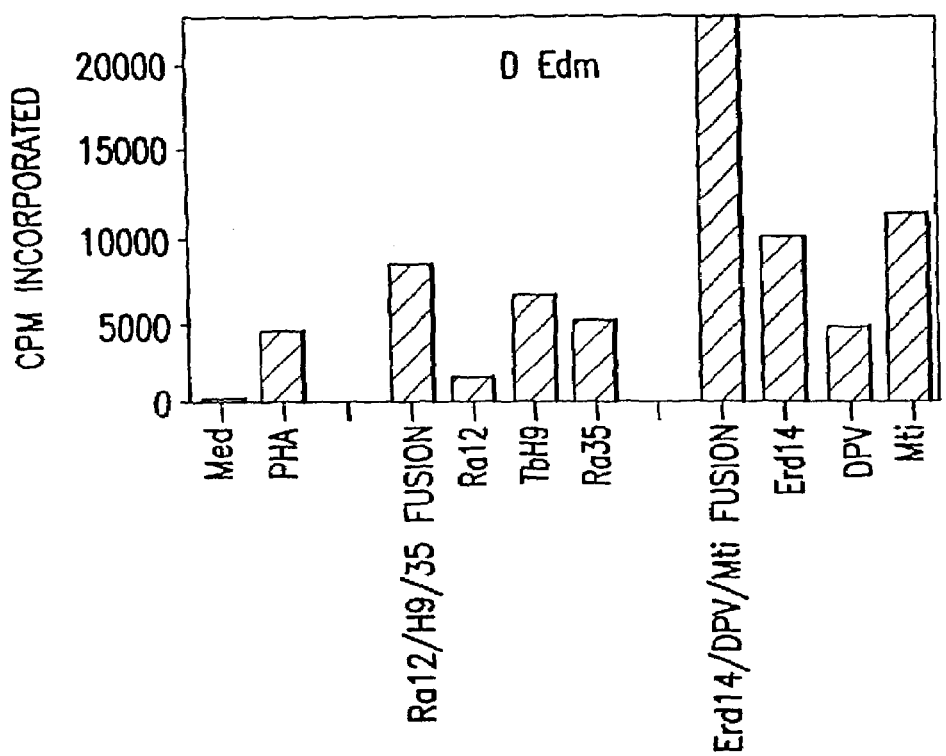
Figure 4A:
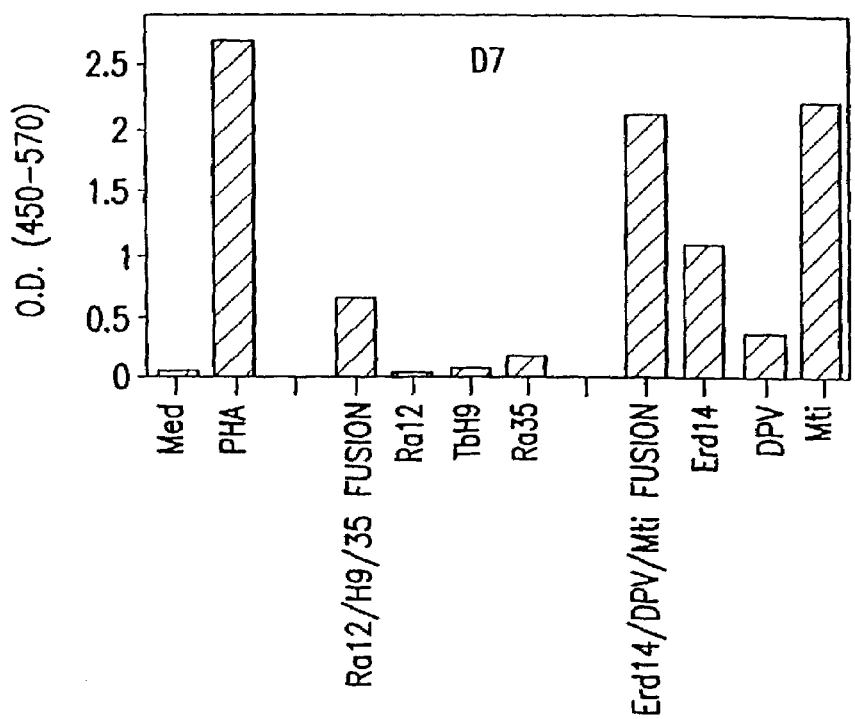
Figure 4B:
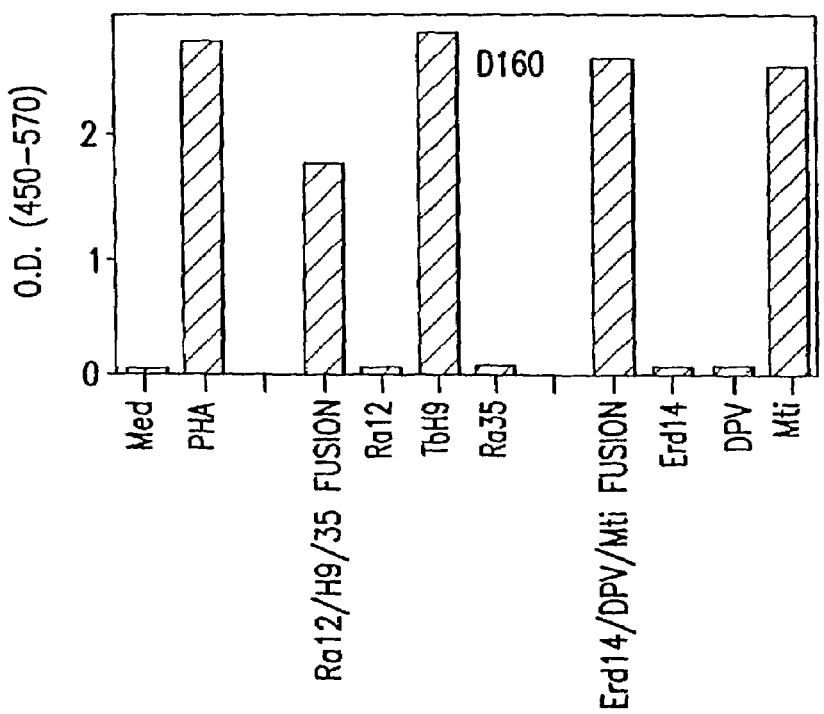
Figure 4C:
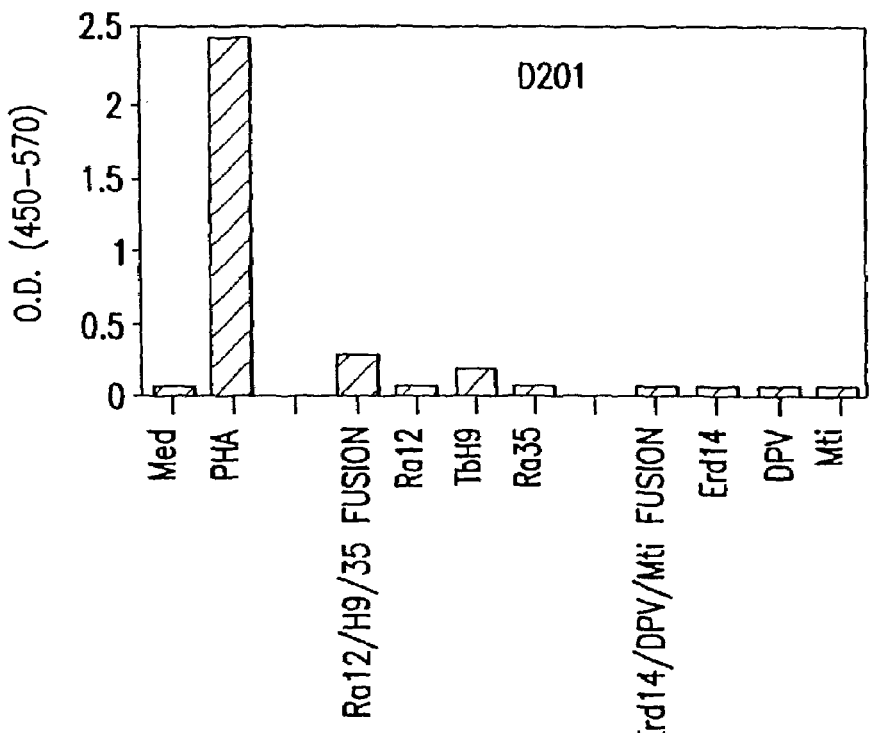
Figure 4D:
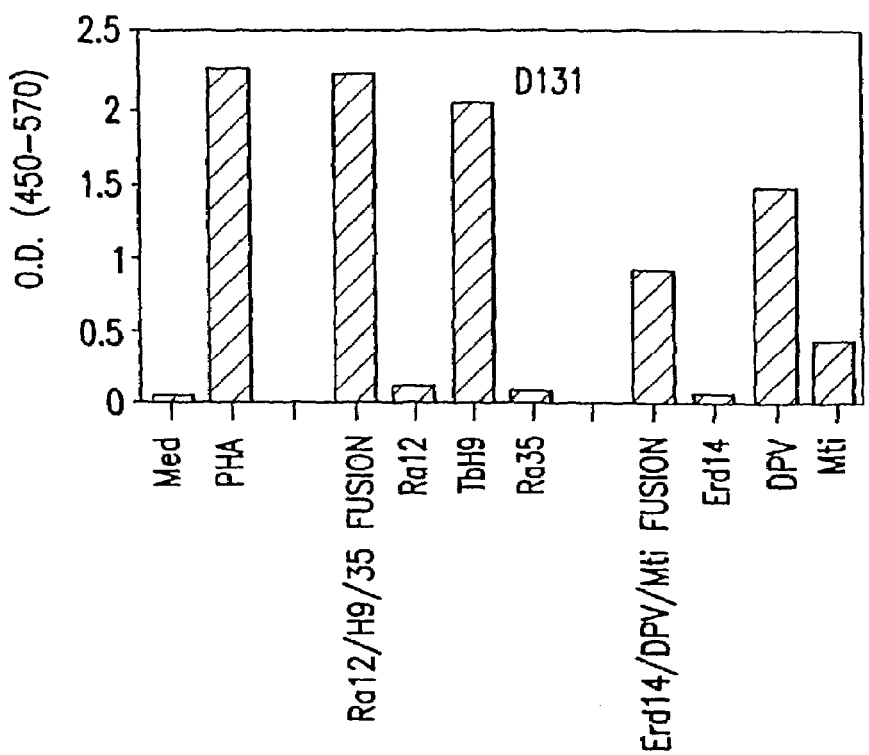
Figure 4E:
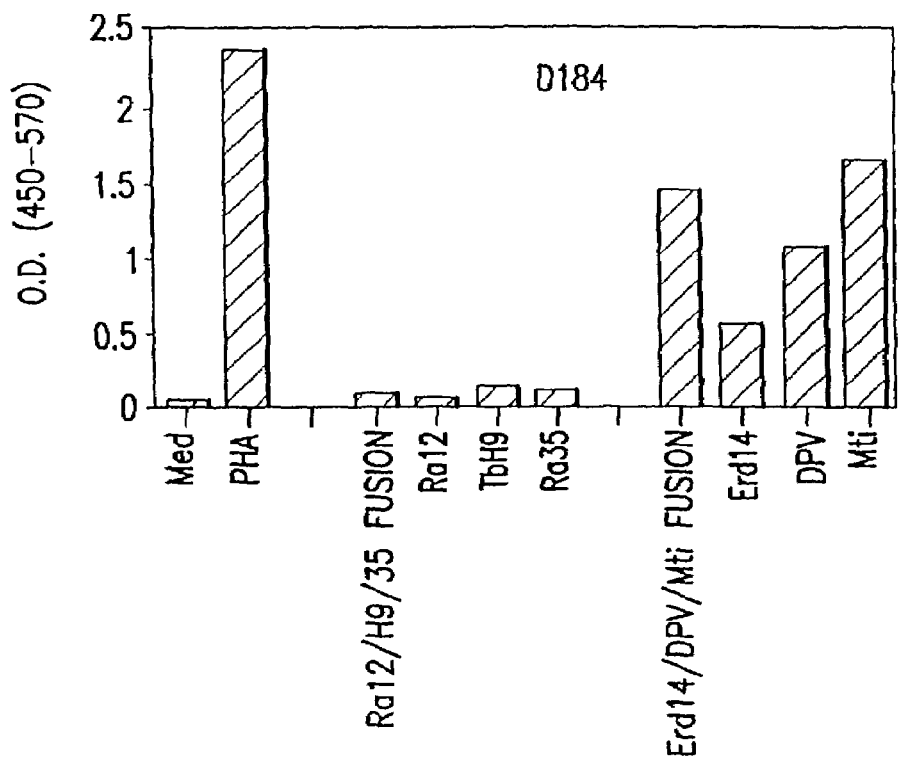
Figure 4F:
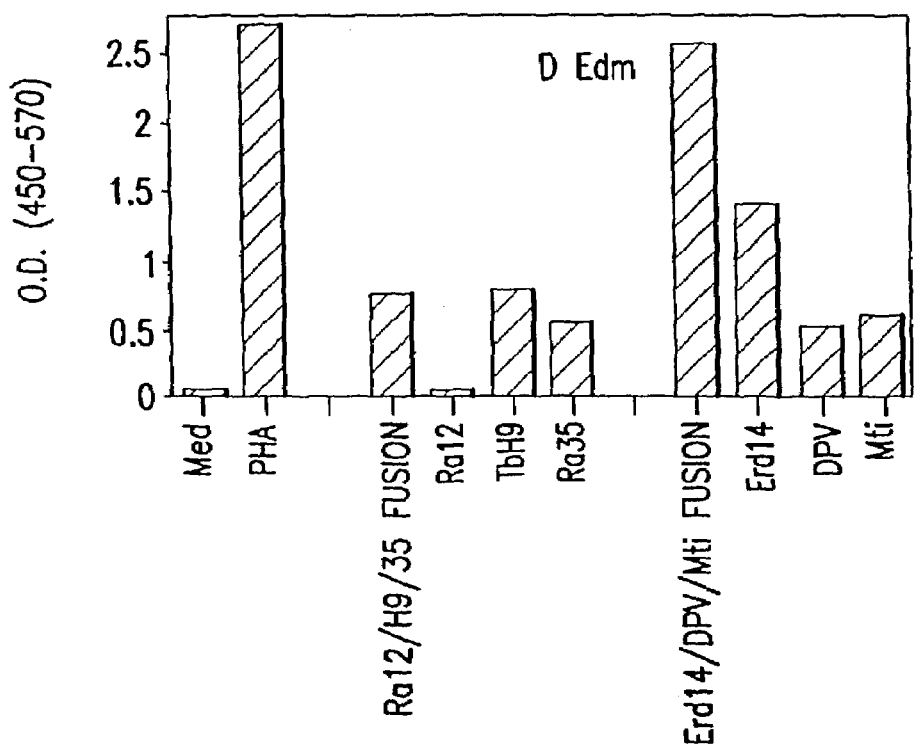

The two fusion proteins were tested for their ability to stimulate T cell responses from six PPD+ subjects. When T cell proliferation was measured, both fusion proteins exhibited a similar reactivity pattern as their individual components (FIG. 3A–3F). A similar result was obtained when IFN-γ production was measured (FIG. 4A–4F). For example, subject D160 responded to antigens TbH9 and MTI individually. Subject D160 also responded to the fusion proteins that contained these antigens (FIGS. 3B and 4B). In contrast, no T cell response from D160 was observed to other antigens individually. Another subject, D201, who did not react with antigens Erd14, DPV or MTI individually, was also unresponsive to the fusion protein containing these antigens. It should be noted that when the T cell responses to the individual components of the two fusion proteins were not particularly strong, the fusion proteins stimulated responses that were equal to or higher than that induced by the individual antigens in most cases.

The Ra12-TbH9-Ra35 tri-fusion protein was also tested as an immunogen in vivo. In these experiments, the fusion protein was injected into the footpads of mice for immunization. Each group of three mice received the protein in a different adjuvant formulation: SBAS1c, SBAS2 (Ling et al., 1997, Vaccine 15:1562–1567), SBAS7 and AL(OH)$_3$. After two subcutaneous immunizations at three week intervals, the animals were sacrificed one week later, and their draining lymph nodes were harvested for use as responder cells in T cell proliferation and cytokine production assays.

Figure 5A:
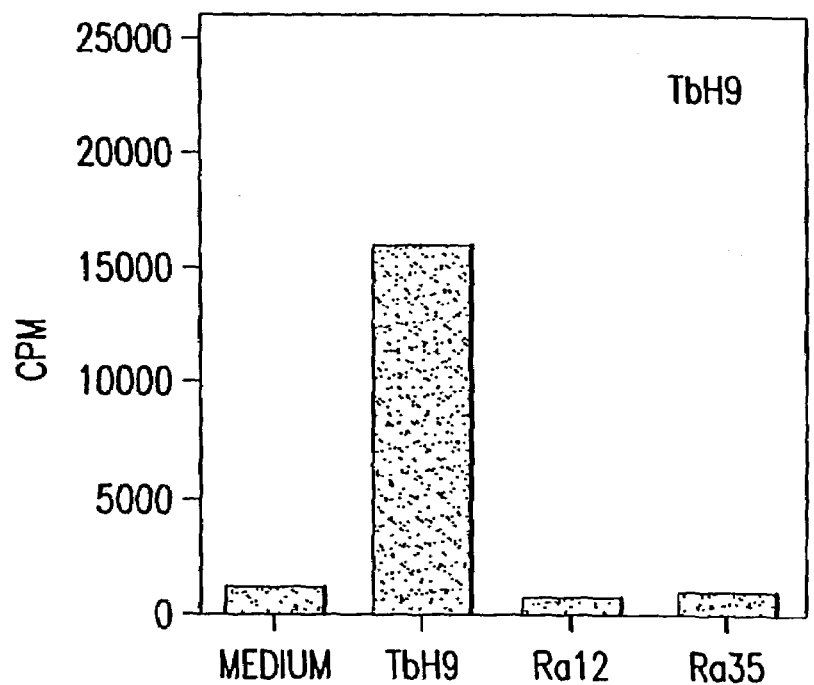
Figure 5B:
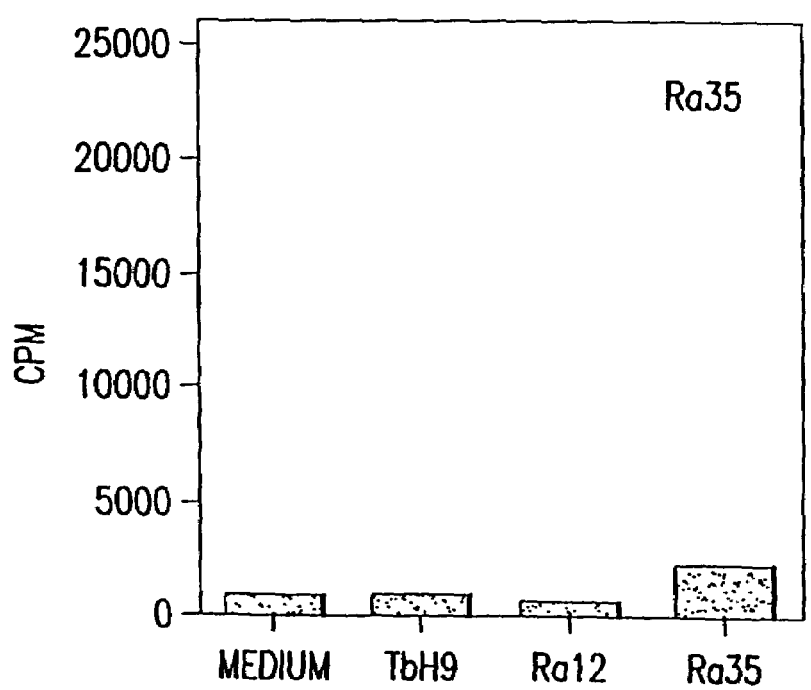
Figure 5C:
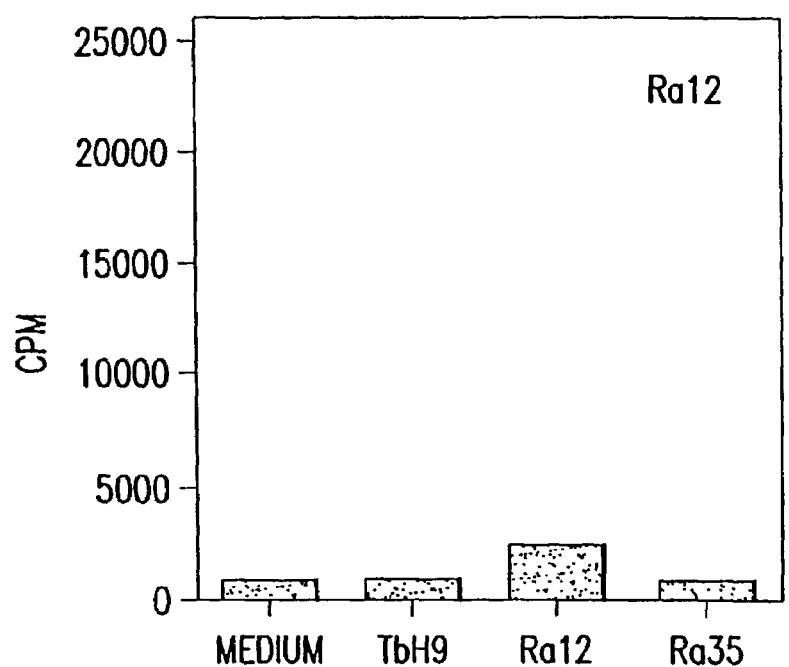
Figure 5D:
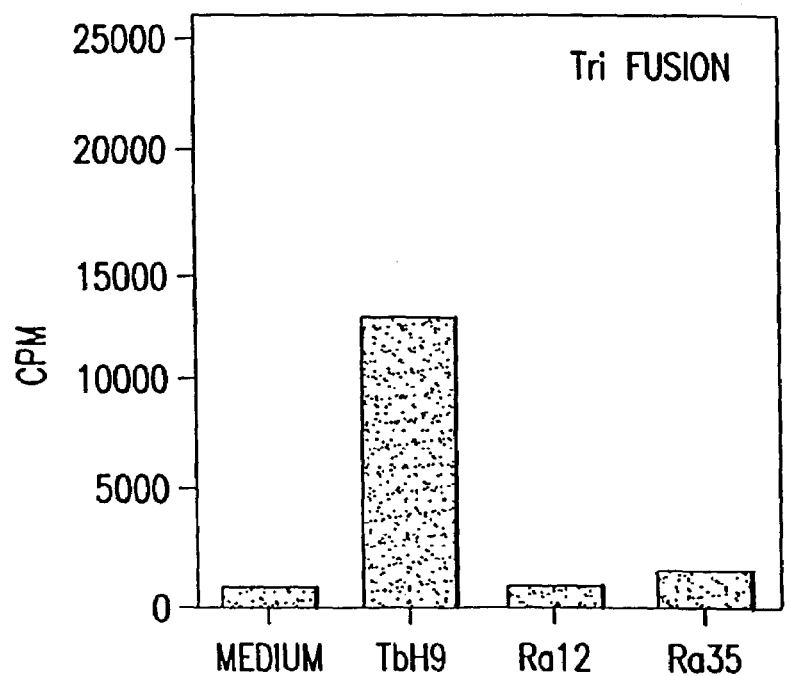
Figure 5E:
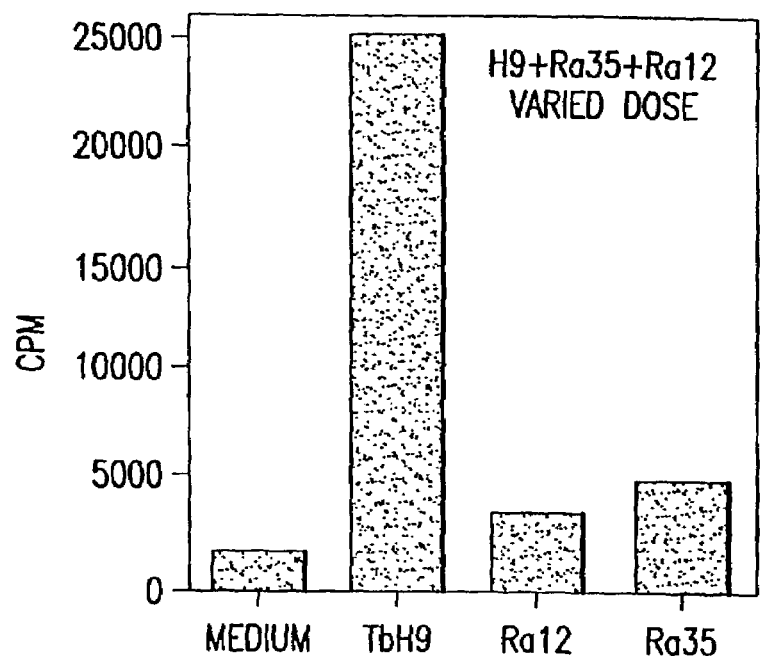
Figure 5F:
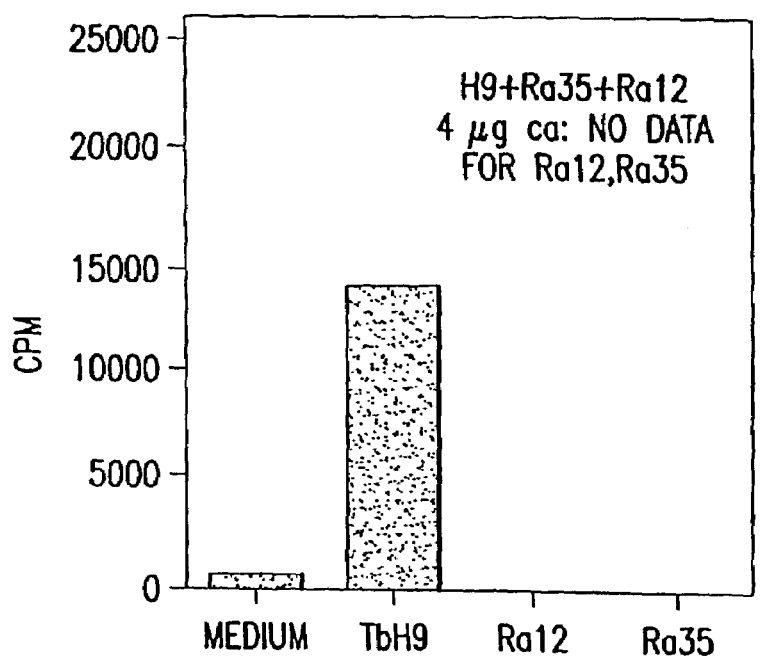

Regardless which adjuvant was used in the immunization, strong T cell proliferation responses were induced against TbH9 when it was used as an individual antigen (FIG. 5A). Weaker responses were induced against Ra35 and Ra12 (FIGS. 5B and 5C). When the Ra12-TbH9-Ra35 fusion protein was used as immunogen, a response similar to that against the individual components was observed.

When cytokine production was measured, adjuvants SBAS1c and SBAS2 produced similar IFN-γ (FIG. 6) and IL-4 responses (FIG. 7). However, the combination of SBAS7 and aluminum hydroxide produced the strongest IFN-γ responses and the lowest level of IL-4 production for all three antigens. With respect to the humoral antibody response in vivo, FIG. 8A–8F shows that the fusion protein elicited both $IgG_1$ and $IgG_{2a}$ antigen-specific responses when it was used with any of the three adjuvants.

Additionally, C57BL/6 mice were immunized with a combination of two expression constructs each containing Mtb32A or Mtb39A coding sequence as DNA vaccines. The immunized animals exhibited significant protection against tuberculosis upon a subsequent aerosol challenge of live bacteria. Based on these results, a fusion construct of Mtb32A and Mtb39A coding sequences was made, and its encoded product tested in a guinea pig long term protection model. In these studies, guinea pigs were immunized with a single recombinant fusion protein or a mixture of Mtb32A and Mtb39A proteins in formulations containing an adjuvant. FIG. 9A–9C shows that guinea pigs immunized with the fusion protein in SBAS1c or SBAS2 were better protected against the development of tuberculosis upon subsequent challenge, as compared to animals immunized with the two antigens in a mixture in the same adjuvant formulation. The fusion protein in BAS2 formulation afforded the greatest protection in the animals. Thus, fusion proteins of various *M. tuberculosis* antigens may be used as more effective immunogens in vaccine formulations than a mixture of the individual components.

The present invention is not to be limited in scope by the exemplified embodiments which are intended as illustrations of single aspects of the invention, and any clones, nucleotide or amino acid sequences which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims. It is also to be understood that all base pair sizes given for nucleotides are approximate and are used for purposes of description.

All publications cited herein are incorporated by reference in their entirety.

What is claimed is:

1. An isolated polynucleotide that encodes a polypeptide comprising the amino acid sequence of SEQ ID NO:2.

2. A composition comprising the polynucleotide of claim 1 and a physiologically acceptable carrier.

3. An expression vector comprising the polynucleotide of claim 1.

4. The expression vector of claim 3, wherein the expression vector is an adenoviral vector.

5. A host cell comprising the expression vector of claim 3.

6. The host cell of claim 5, wherein the host cell is a eukaryote.

7. The host cell of claim 5, wherein the host cell is a prokaryote.

8. The host cell of claim 7, wherein the host cell is *Bacillus-Calmette-Guerrin*.

9. A method of recombinantly making a polypeptide encoded by the polynucleotide of claim 1, the method comprising the step of expressing the polynucleotide of claim 1 in a host cell.

* * * * *

UNITED STATES PATENT AND TRADEMARK OFFICE
CERTIFICATE OF CORRECTION

PATENT NO.       : 7,064,195 B2
APPLICATION NO.  : 10/359459
DATED            : June 20, 2006
INVENTOR(S)      : Skeiky et al.

It is certified that error appears in the above-identified patent and that said Letters Patent is hereby corrected as shown below:

In FIG. 1A, please delete the line directly below the line ending with 570,

"G A L R P E I N S A R M Y A G P G S A S L V A A A C M W D S V"

and insert,

--G A L P P E I N S A R M Y A G P G S A S L V A A A Q M W D S V--

In FIG. 1B, please delete the line directly below the line ending with 1045,

"T A T L L P F E E A P E M Y S A C G L L E Q A A A V E E A S D T"

and insert,

--T A T L L P F E E A P E M T S A G G L L E Q A A A V E E A S D T--

In FIG. 1B, please delete the line directly below the line ending with 1140,

"A A A N Q L M N N V P Q A L Q Q L A Q P T Q C T T P S S K L G"

and insert,

--A A A N Q L M N N V P Q A L Q Q L A Q P T Q G T T P S S K L G--

In FIG. 1B, please delete the line directly below the line ending with 1710,

"P H S P A A G D I A P P A L S Q Q R F A D F P A L P L D P S A"

and insert,

--P H S P A A G D I A P P A L S Q D R F A D F P A L P L D P S A--

UNITED STATES PATENT AND TRADEMARK OFFICE
CERTIFICATE OF CORRECTION

PATENT NO. : 7,064,195 B2
APPLICATION NO. : 10/359459
DATED : June 20, 2006
INVENTOR(S) : Skeiky et al.

It is certified that error appears in the above-identified patent and that said Letters Patent is hereby corrected as shown below:

In FIG. 1B (continued), please delete the line directly below the line ending with 2280,

"N G L G D V V G M N T A A S"

and insert,

--N G L G Q V V G M N T A A S--

Signed and Sealed this

Thirtieth Day of October, 2007

JON W. DUDAS
*Director of the United States Patent and Trademark Office*

SEQUENCE LISTING

<160> NUMBER OF SEQ ID NOS: 10

<210> SEQ ID NO 1
<211> LENGTH: 2287
<212> TYPE: DNA
<213> ORGANISM: Artificial Sequence
<220> FEATURE:
<223> OTHER INFORMATION: Description of Artificial Sequence:tri-fusion
      protein Ra12-TbH9-Ra35
<220> FEATURE:

-continued

```
<221> NAME/KEY: modified_base
<222> LOCATION: (30)
<223> OTHER INFORMATION: n = g, a, c or t
<220> FEATURE:
<221> NAME/KEY: modified_base
<222> LOCATION: (33)
<223> OTHER INFORMATION: n = g, a, c or t
<220> FEATURE:
<221> NAME/KEY: CDS
<222> LOCATION: (42)..(2231)
<220> FEATURE:
<221> NAME/KEY: modified_base
<222> LOCATION: (2270)
<223> OTHER INFORMATION: n = g, a, c or t

<400> SEQUENCE: 1
tctagaaata attttgttta ctttaagaan ganatataca t atg cat cac cat cac         56
                                            Met His His His His
                                              1               5 cat cac acg gcc gcg tcc gat aac ttc cag ctg tcc cag ggt ggg cag          104
His His Thr Ala Ala Ser Asp Asn Phe Gln Leu Ser Gln Gly Gly Gln
             10                  15                  20 gga ttc gcc att ccg atc ggg cag gcg atg gcg atc gcg ggc cag atc         152
Gly Phe Ala Ile Pro Ile Gly Gln Ala Met Ala Ile Ala Gly Gln Ile
     25                  30                  35 cga tcg ggt ggg ggg tca ccc acc gtt cat atc ggg cct acc gcc ttc         200
Arg Ser Gly Gly Gly Ser Pro Thr Val His Ile Gly Pro Thr Ala Phe
 40                  45                  50 ctc ggc ttg ggt gtt gtc gac aac aac ggc aac ggc gca cga gtc caa         248
Leu Gly Leu Gly Val Val Asp Asn Asn Gly Asn Gly Ala Arg Val Gln
         55                  60                  65 cgc gtg gtc ggg agc gct ccg gcg gca agt ctc ggc atc tcc acc ggc         296
Arg Val Val Gly Ser Ala Pro Ala Ala Ser Leu Gly Ile Ser Thr Gly
 70                  75                  80                  85 gac gtg atc acc gcg gtc gac ggc gct ccg atc aac tcg gcc acc gcg         344
Asp Val Ile Thr Ala Val Asp Gly Ala Pro Ile Asn Ser Ala Thr Ala
             90                  95                 100 atg gcg gac gcg ctt aac ggg cat cat ccc ggt gac gtc atc tcg gtg         392
Met Ala Asp Ala Leu Asn Gly His His Pro Gly Asp Val Ile Ser Val
        105                 110                 115 acc tgg caa acc aag tcg ggc ggc acg cgt aca ggg aac gtg aca ttg         440
Thr Trp Gln Thr Lys Ser Gly Gly Thr Arg Thr Gly Asn Val Thr Leu
    120                 125                 130 gcc gag gga ccc ccg gcc gaa ttc atg gtg gat ttc ggg gcg tta cca         488
Ala Glu Gly Pro Pro Ala Glu Phe Met Val Asp Phe Gly Ala Leu Pro
135                 140                 145 ccg gag atc aac tcc gcg agg atg tac gcc ggc ccg ggt tcg gcc tcg         536
Pro Glu Ile Asn Ser Ala Arg Met Tyr Ala Gly Pro Gly Ser Ala Ser
150                 155                 160                 165 ctg gtg gcc gcg gct cag atg tgg gac agc gtg gcg agt gac ctg ttt         584
Leu Val Ala Ala Ala Gln Met Trp Asp Ser Val Ala Ser Asp Leu Phe
            170                 175                 180 tcg gcc gcg tcg gcg ttt cag tcg gtg gtc tgg ggt ctg acg gtg ggg         632
Ser Ala Ala Ser Ala Phe Gln Ser Val Val Trp Gly Leu Thr Val Gly
        185                 190                 195 tcg tgg ata ggt tcg tcg gcg ggt ctg atg gtg gcg gcg gcc tcg ccg         680
Ser Trp Ile Gly Ser Ser Ala Gly Leu Met Val Ala Ala Ala Ser Pro
    200                 205                 210 tat gtg gcg tgg atg agc gtc acc gcg ggg cag gcc gag ctg acc gcc         728
Tyr Val Ala Trp Met Ser Val Thr Ala Gly Gln Ala Glu Leu Thr Ala
215                 220                 225 gcc cag gtc cgg gtt gct gcg gcg gcc tac gag acg gcg tat ggg ctg         776
Ala Gln Val Arg Val Ala Ala Ala Ala Tyr Glu Thr Ala Tyr Gly Leu
```

```
                                                            -continued 230             235             240             245 acg gtg ccc ccg ccg gtg atc gcc gag aac cgt gct gaa ctg atg att      824
Thr Val Pro Pro Pro Val Ile Ala Glu Asn Arg Ala Glu Leu Met Ile
                250             255             260 ctg ata gcg acc aac ctc ttg ggg caa aac acc ccg gcg atc gcg gtc      872
Leu Ile Ala Thr Asn Leu Leu Gly Gln Asn Thr Pro Ala Ile Ala Val
                265             270             275 aac gag gcc gaa tac ggc gag atg tgg gcc caa gac gcc gcc gcg atg      920
Asn Glu Ala Glu Tyr Gly Glu Met Trp Ala Gln Asp Ala Ala Ala Met
                280             285             290 ttt ggc tac gcc gcg gcg acg gcg acg gcg acg gcg acg ttg ctg ccg      968
Phe Gly Tyr Ala Ala Ala Thr Ala Thr Ala Thr Ala Thr Leu Leu Pro
        295             300             305 ttc gag gag gcg ccg gag atg acc agc gcg ggt ggg ctc ctc gag cag     1016
Phe Glu Glu Ala Pro Glu Met Thr Ser Ala Gly Gly Leu Leu Glu Gln
        310             315             320             325 gcc gcc gcg gtc gag gag gcc tcc gac acc gcc gcg aac cag ttg         1064
Ala Ala Ala Val Glu Glu Ala Ser Asp Thr Ala Ala Ala Asn Gln Leu
                330             335             340 atg aac aat gtg ccc cag gcg ctg caa cag ctg gcc cag ccc acg cag     1112
Met Asn Asn Val Pro Gln Ala Leu Gln Gln Leu Ala Gln Pro Thr Gln
                345             350             355 ggc acc acg cct tct tcc aag ctg ggt ggc ctg tgg aag acg gtc tcg     1160
Gly Thr Thr Pro Ser Ser Lys Leu Gly Gly Leu Trp Lys Thr Val Ser
                360             365             370 ccg cat cgg tcg ccg atc agc aac atg gtg tcg atg gcc aac aac cac     1208
Pro His Arg Ser Pro Ile Ser Asn Met Val Ser Met Ala Asn Asn His
        375             380             385 atg tcg atg acc aac tcg ggt gtg tcg atg acc aac acc ttg agc tcg     1256
Met Ser Met Thr Asn Ser Gly Val Ser Met Thr Asn Thr Leu Ser Ser
390             395             400             405 atg ttg aag ggc ttt gct ccg gcg gcg gcc cgc cag gcc gtg caa acc     1304
Met Leu Lys Gly Phe Ala Pro Ala Ala Ala Arg Gln Ala Val Gln Thr
                410             415             420 gcg gcg caa aac ggg gtc cgg gcg atg agc tcg ctg ggc agc tcg ctg     1352
Ala Ala Gln Asn Gly Val Arg Ala Met Ser Ser Leu Gly Ser Ser Leu
                425             430             435 ggt tct tcg ggt ctg ggc ggt ggg gtg gcc gcc aac ttg ggt cgg gcg     1400
Gly Ser Ser Gly Leu Gly Gly Gly Val Ala Ala Asn Leu Gly Arg Ala
                440             445             450 gcc tcg gtc ggt tcg ttg tcg gtg ccg cag gcc tgg gcc gcg gcc aac     1448
Ala Ser Val Gly Ser Leu Ser Val Pro Gln Ala Trp Ala Ala Ala Asn
455             460             465 cag gca gtc acc ccg gcg gcg cgg gcg ctg ccg ctg acc agc ctg acc     1496
Gln Ala Val Thr Pro Ala Ala Arg Ala Leu Pro Leu Thr Ser Leu Thr
470             475             480             485 agc gcc gcg gaa aga ggg ccc ggg cag atg ctg ggc ggg ctg ccg gtg     1544
Ser Ala Ala Glu Arg Gly Pro Gly Gln Met Leu Gly Gly Leu Pro Val
                490             495             500 ggg cag atg ggc gcc agg gcc ggt ggt ggg ctc agt ggt gtg ctg cgt     1592
Gly Gln Met Gly Ala Arg Ala Gly Gly Gly Leu Ser Gly Val Leu Arg
                505             510             515 gtt ccg ccg cga ccc tat gtg atg ccg cat tct ccg gca gcc ggc gat     1640
Val Pro Pro Arg Pro Tyr Val Met Pro His Ser Pro Ala Ala Gly Asp
                520             525             530 atc gcc ccg ccg gcc ttg tcg cag gac cgg ttc gcc gac ttc ccc gcg     1688
Ile Ala Pro Pro Ala Leu Ser Gln Asp Arg Phe Ala Asp Phe Pro Ala
535             540             545 ctg ccc ctc gac ccg tcc gcg atg gtc gcc caa gtg ggg cca cag gtg     1736
```

-continued

```
Leu Pro Leu Asp Pro Ser Ala Met Val Ala Gln Val Gly Pro Gln Val
550                 555                 560                 565 gtc aac atc aac acc aaa ctg ggc tac aac aac gcc gtg ggc gcc ggg    1784
Val Asn Ile Asn Thr Lys Leu Gly Tyr Asn Asn Ala Val Gly Ala Gly
                570                 575                 580 acc ggc atc gtc atc gat ccc aac ggt gtc gtg ctg acc aac aac cac    1832
Thr Gly Ile Val Ile Asp Pro Asn Gly Val Val Leu Thr Asn Asn His
            585                 590                 595 gtg atc gcg ggc gcc acc gac atc aat gcg ttc agc gtc ggc tcc ggc    1880
Val Ile Ala Gly Ala Thr Asp Ile Asn Ala Phe Ser Val Gly Ser Gly
        600                 605                 610 caa acc tac ggc gtc gat gtg gtc ggg tat gac cgc acc cag gat gtc    1928
Gln Thr Tyr Gly Val Asp Val Val Gly Tyr Asp Arg Thr Gln Asp Val
    615                 620                 625 gcg gtg ctg cag ctg cgc ggt gcc ggt ggc ctg ccg tcg gcg gcg atc    1976
Ala Val Leu Gln Leu Arg Gly Ala Gly Gly Leu Pro Ser Ala Ala Ile
630                 635                 640                 645 ggt ggc ggc gtc gcg gtt ggt gag ccc gtc gtc gcg atg ggc aac agc    2024
Gly Gly Gly Val Ala Val Gly Glu Pro Val Val Ala Met Gly Asn Ser
                650                 655                 660 ggt ggg cag ggc gga acg ccc cgt gcg gtg cct ggc agg gtg gtc gcg    2072
Gly Gly Gln Gly Gly Thr Pro Arg Ala Val Pro Gly Arg Val Val Ala
            665                 670                 675 ctc ggc caa acc gtg cag gcg tcg gat tcg ctg acc ggt gcc gaa gag    2120
Leu Gly Gln Thr Val Gln Ala Ser Asp Ser Leu Thr Gly Ala Glu Glu
        680                 685                 690 aca ttg aac ggg ttg atc cag ttc gat gcc gcg atc cag ccc ggt gat    2168
Thr Leu Asn Gly Leu Ile Gln Phe Asp Ala Ala Ile Gln Pro Gly Asp
    695                 700                 705 tcg ggc ggg ccc gtc gtc aac ggc cta gga cag gtg gtc ggt atg aac    2216
Ser Gly Gly Pro Val Val Asn Gly Leu Gly Gln Val Val Gly Met Asn
710                 715                 720                 725 acg gcc gcg tcc taggatatcc atcacactgg cggccgctcg agcagatccg        2268
Thr Ala Ala Ser gntgtaacaa agcccgaaa                                                2287
```

<210> SEQ ID NO 2
<211> LENGTH: 729
<212> TYPE: PRT
<213> ORGANISM: Artificial Sequence
<220> FEATURE:
<223> OTHER INFORMATION: Description of Artificial Sequence:tri-fusion

<400> SEQUENCE: 2

```
Met His His His His His Thr Ala Ala Ser Asp Asn Phe Gln Leu
1               5                   10                  15

Ser Gln Gly Gly Gln Gly Phe Ala Ile Pro Ile Gly Gln Ala Met Ala
                20                  25                  30

Ile Ala Gly Gln Ile Arg Ser Gly Gly Ser Pro Thr Val His Ile
            35                  40                  45

Gly Pro Thr Ala Phe Leu Gly Leu Gly Val Val Asp Asn Asn Gly Asn
        50                  55                  60

Gly Ala Arg Val Gln Arg Val Val Gly Ser Ala Pro Ala Ala Ser Leu
65                  70                  75                  80

Gly Ile Ser Thr Gly Asp Val Ile Thr Ala Val Asp Gly Ala Pro Ile
                85                  90                  95

Asn Ser Ala Thr Ala Met Ala Asp Ala Leu Asn Gly His His Pro Gly
            100                 105                 110
```

-continued

```
Asp Val Ile Ser Val Thr Trp Gln Thr Lys Ser Gly Gly Thr Arg Thr
            115                 120                 125

Gly Asn Val Thr Leu Ala Glu Gly Pro Ala Glu Phe Met Val Asp
        130                 135                 140

Phe Gly Ala Leu Pro Pro Glu Ile Asn Ser Ala Arg Met Tyr Ala Gly
145                 150                 155                 160

Pro Gly Ser Ala Ser Leu Val Ala Ala Gln Met Trp Asp Ser Val
            165                 170                 175

Ala Ser Asp Leu Phe Ser Ala Ser Ala Phe Gln Ser Val Val Trp
            180                 185                 190

Gly Leu Thr Val Gly Ser Trp Ile Gly Ser Ser Ala Gly Leu Met Val
            195                 200                 205

Ala Ala Ala Ser Pro Tyr Val Ala Trp Met Ser Val Thr Ala Gly Gln
            210                 215                 220

Ala Glu Leu Thr Ala Ala Gln Val Arg Val Ala Ala Ala Tyr Glu
225                 230                 235                 240

Thr Ala Tyr Gly Leu Thr Val Pro Pro Val Ile Ala Glu Asn Arg
            245                 250                 255

Ala Glu Leu Met Ile Leu Ile Ala Thr Asn Leu Leu Gly Gln Asn Thr
            260                 265                 270

Pro Ala Ile Ala Val Asn Glu Ala Glu Tyr Gly Glu Met Trp Ala Gln
            275                 280                 285

Asp Ala Ala Ala Met Phe Gly Tyr Ala Ala Ala Thr Ala Thr Ala Thr
            290                 295                 300

Ala Thr Leu Leu Pro Phe Glu Glu Ala Pro Glu Met Thr Ser Ala Gly
305                 310                 315                 320

Gly Leu Leu Glu Gln Ala Ala Ala Val Glu Glu Ala Ser Asp Thr Ala
            325                 330                 335

Ala Ala Asn Gln Leu Met Asn Asn Val Pro Gln Ala Leu Gln Gln Leu
            340                 345                 350

Ala Gln Pro Thr Gln Gly Thr Thr Pro Ser Ser Lys Leu Gly Gly Leu
            355                 360                 365

Trp Lys Thr Val Ser Pro His Arg Ser Pro Ile Ser Asn Met Val Ser
            370                 375                 380

Met Ala Asn Asn His Met Ser Met Thr Asn Ser Gly Val Ser Met Thr
385                 390                 395                 400

Asn Thr Leu Ser Ser Met Leu Lys Gly Phe Ala Pro Ala Ala Ala Arg
            405                 410                 415

Gln Ala Val Gln Thr Ala Ala Gln Asn Gly Val Arg Ala Met Ser Ser
            420                 425                 430

Leu Gly Ser Ser Leu Gly Ser Ser Gly Leu Gly Gly Val Ala Ala
            435                 440                 445

Asn Leu Gly Arg Ala Ala Ser Val Gly Ser Leu Ser Val Pro Gln Ala
            450                 455                 460

Trp Ala Ala Ala Asn Gln Ala Val Thr Pro Ala Ala Arg Ala Leu Pro
465                 470                 475                 480

Leu Thr Ser Leu Thr Ser Ala Ala Glu Arg Gly Pro Gly Gln Met Leu
            485                 490                 495

Gly Gly Leu Pro Val Gly Gln Met Gly Ala Arg Ala Gly Gly Leu
            500                 505                 510

Ser Gly Val Leu Arg Val Pro Pro Arg Pro Tyr Val Met Pro His Ser
            515                 520                 525
```

```
Pro Ala Ala Gly Asp Ile Ala Pro Pro Ala Leu Ser Gln Asp Arg Phe
        530                 535                 540

Ala Asp Phe Pro Ala Leu Pro Leu Asp Pro Ser Ala Met Val Ala Gln
545                 550                 555                 560

Val Gly Pro Gln Val Val Asn Ile Asn Thr Lys Leu Gly Tyr Asn Asn
                565                 570                 575

Ala Val Gly Ala Gly Thr Gly Ile Val Ile Asp Pro Asn Gly Val Val
            580                 585                 590

Leu Thr Asn Asn His Val Ile Ala Gly Ala Thr Asp Ile Asn Ala Phe
        595                 600                 605

Ser Val Gly Ser Gly Gln Thr Tyr Gly Val Asp Val Val Gly Tyr Asp
    610                 615                 620

Arg Thr Gln Asp Val Ala Val Leu Gln Leu Arg Gly Ala Gly Gly Leu
625                 630                 635                 640

Pro Ser Ala Ala Ile Gly Gly Val Ala Val Gly Glu Pro Val Val
                645                 650                 655

Ala Met Gly Asn Ser Gly Gly Gln Gly Gly Thr Pro Arg Ala Val Pro
            660                 665                 670

Gly Arg Val Val Ala Leu Gly Gln Thr Val Gln Ala Ser Asp Ser Leu
        675                 680                 685

Thr Gly Ala Glu Glu Thr Leu Asn Gly Leu Ile Gln Phe Asp Ala Ala
    690                 695                 700

Ile Gln Pro Gly Asp Ser Gly Gly Pro Val Val Asn Gly Leu Gly Gln
705                 710                 715                 720

Val Val Gly Met Asn Thr Ala Ala Ser
                725

<210> SEQ ID NO 3
<211> LENGTH: 1081
<212> TYPE: DNA
<213> ORGANISM: Artificial Sequence
<220> FEATURE:
<223> OTHER INFORMATION: Description of Artificial Sequence:tri-fusion
      protein Erd14-DPV-MTI
<220> FEATURE:
<221> NAME/KEY: CDS
<222> LOCATION: (10)..(1002)

<400> SEQUENCE: 3 gatatacat atg cat cac cat cac cat cac atg gcc acc acc ctt ccc gtt    51
          Met His His His His His His Met Ala Thr Thr Leu Pro Val
            1               5                  10 cag cgc cac ccg cgg tcc ctc ttc ccc gag ttt tct gag ctg ttc gcg     99
Gln Arg His Pro Arg Ser Leu Phe Pro Glu Phe Ser Glu Leu Phe Ala
 15                  20                  25                  30 gcc ttc ccg tca ttc gcc gga ctc cgg ccc acc ttc gac acc cgg ttg    147
Ala Phe Pro Ser Phe Ala Gly Leu Arg Pro Thr Phe Asp Thr Arg Leu
                 35                  40                  45 atg cgg ctg gaa gac gag atg aaa gag ggg cgc tac gag gta cgc gcg    195
Met Arg Leu Glu Asp Glu Met Lys Glu Gly Arg Tyr Glu Val Arg Ala
             50                  55                  60 gag ctt ccc ggg gtc gac ccc gac aag gac gtc gac att atg gtc cgc    243
Glu Leu Pro Gly Val Asp Pro Asp Lys Asp Val Asp Ile Met Val Arg
         65                  70                  75 gat ggt cag ctg acc atc aag gcc gag cgc acc gag cag aag gac ttc    291
Asp Gly Gln Leu Thr Ile Lys Ala Glu Arg Thr Glu Gln Lys Asp Phe
     80                  85                  90
```

|  |  |
|---|---|
| gac ggt cgc tcg gaa ttc gcg tac ggt tcc ttc gtt cgc acg gtg tcg<br>Asp Gly Arg Ser Glu Phe Ala Tyr Gly Ser Phe Val Arg Thr Val Ser<br>95                              100                       105                     110 | 339 |
| ctg ccg gta ggt gct gac gag gac gac att aag gcc acc tac gac aag<br>Leu Pro Val Gly Ala Asp Glu Asp Asp Ile Lys Ala Thr Tyr Asp Lys<br>                   115                     120                   125 | 387 |
| ggc att ctt act gtg tcg gtg gcg gtt tcg gaa ggg aag cca acc gaa<br>Gly Ile Leu Thr Val Ser Val Ala Val Ser Glu Gly Lys Pro Thr Glu<br>              130                     135                    140 | 435 |
| aag cac att cag atc cgg tcc acc aac aag ctt gat ccc gtg gac gcg<br>Lys His Ile Gln Ile Arg Ser Thr Asn Lys Leu Asp Pro Val Asp Ala<br>145                              150                     155 | 483 |
| gtc att aac acc acc tgc aat tac ggg cag gta gta gct gcg ctc aac<br>Val Ile Asn Thr Thr Cys Asn Tyr Gly Gln Val Val Ala Ala Leu Asn<br>           160                     165                    170 | 531 |
| gcg acg gat ccg ggg gct gcc gca cag ttc aac gcc tca ccg gtg gcg<br>Ala Thr Asp Pro Gly Ala Ala Ala Gln Phe Asn Ala Ser Pro Val Ala<br>175                              180                     185                   190 | 579 |
| cag tcc tat ttg cgc aat ttc ctc gcc gca ccg cca cct cag cgc gct<br>Gln Ser Tyr Leu Arg Asn Phe Leu Ala Ala Pro Pro Pro Gln Arg Ala<br>                   195                     200                   205 | 627 |
| gcc atg gcc gcg caa ttg caa gct gtg ccg ggg gcg gca cag tac atc<br>Ala Met Ala Ala Gln Leu Gln Ala Val Pro Gly Ala Ala Gln Tyr Ile<br>              210                     215                    220 | 675 |
| ggc ctt gtc gag tcg gtt gcc ggc tcc tgc aac aac tat gag ctc atg<br>Gly Leu Val Glu Ser Val Ala Gly Ser Cys Asn Asn Tyr Glu Leu Met<br>225                              230                     235 | 723 |
| acg att aat tac cag ttc ggg gac gtc gac gct cat ggc gcc atg atc<br>Thr Ile Asn Tyr Gln Phe Gly Asp Val Asp Ala His Gly Ala Met Ile<br>           240                     245                    250 | 771 |
| cgc gct cag gcg gcg tcg ctt gag gcg gag cat cag gcc atc gtt cgt<br>Arg Ala Gln Ala Ala Ser Leu Glu Ala Glu His Gln Ala Ile Val Arg<br>255                              260                     265                   270 | 819 |
| gat gtg ttg gcc gcg ggt gac ttt tgg ggc ggc gcc ggt tcg gtg gct<br>Asp Val Leu Ala Ala Gly Asp Phe Trp Gly Gly Ala Gly Ser Val Ala<br>                   275                     280                   285 | 867 |
| tgc cag gag ttc att acc cag ttg ggc cgt aac ttc cag gtg atc tac<br>Cys Gln Glu Phe Ile Thr Gln Leu Gly Arg Asn Phe Gln Val Ile Tyr<br>              290                     295                    300 | 915 |
| gag cag gcc aac gcc cac ggg cag aag gtg cag gct gcc ggc aac aac<br>Glu Gln Ala Asn Ala His Gly Gln Lys Val Gln Ala Ala Gly Asn Asn<br>305                              310                     315 | 963 |
| atg gcg caa acc gac agc gcc gtc ggc tcc agc tgg gcc actagtaacg<br>Met Ala Gln Thr Asp Ser Ala Val Gly Ser Ser Trp Ala<br>320                              325                     330 | 1012 |
| gccgccagtg tgctggaatt ctgcagatat ccatcacact ggcggccgct cgagcagatc | 1072 |
| cggctgcta | 1081 |

<210> SEQ ID NO 4
<211> LENGTH: 331
<212> TYPE: PRT
<213> ORGANISM: Artificial Sequence
<220> FEATURE:
<223> OTHER INFORMATION: Description of Artificial Sequence:tri-fusion

```
<400> SEQUENCE: 4

Met His His His His His Met Ala Thr Thr Leu Pro Val Gln Arg
  1               5                  10                  15

His Pro Arg Ser Leu Phe Pro Glu Phe Ser Glu Leu Phe Ala Ala Phe
             20                  25                  30

Pro Ser Phe Ala Gly Leu Arg Pro Thr Phe Asp Thr Arg Leu Met Arg
         35                  40                  45

Leu Glu Asp Glu Met Lys Glu Gly Arg Tyr Glu Val Arg Ala Glu Leu
 50                  55                  60

Pro Gly Val Asp Pro Asp Lys Asp Val Asp Ile Met Val Arg Asp Gly
 65                  70                  75                  80

Gln Leu Thr Ile Lys Ala Glu Arg Thr Glu Gln Lys Asp Phe Asp Gly
                 85                  90                  95

Arg Ser Glu Phe Ala Tyr Gly Ser Phe Val Arg Thr Val Ser Leu Pro
                100                 105                 110

Val Gly Ala Asp Glu Asp Asp Ile Lys Ala Thr Tyr Asp Lys Gly Ile
            115                 120                 125

Leu Thr Val Ser Val Ala Val Ser Glu Gly Lys Pro Thr Glu Lys His
130                 135                 140

Ile Gln Ile Arg Ser Thr Asn Lys Leu Asp Pro Val Asp Ala Val Ile
145                 150                 155                 160

Asn Thr Thr Cys Asn Tyr Gly Gln Val Val Ala Ala Leu Asn Ala Thr
                165                 170                 175

Asp Pro Gly Ala Ala Gln Phe Asn Ala Ser Pro Val Ala Gln Ser
            180                 185                 190

Tyr Leu Arg Asn Phe Leu Ala Ala Pro Pro Gln Arg Ala Ala Met
            195                 200                 205

Ala Ala Gln Leu Gln Ala Val Pro Gly Ala Ala Gln Tyr Ile Gly Leu
            210                 215                 220

Val Glu Ser Val Ala Gly Ser Cys Asn Asn Tyr Glu Leu Met Thr Ile
225                 230                 235                 240

Asn Tyr Gln Phe Gly Asp Val Asp Ala His Gly Ala Met Ile Arg Ala
                245                 250                 255

Gln Ala Ala Ser Leu Glu Ala Glu His Gln Ala Ile Val Arg Asp Val
            260                 265                 270

Leu Ala Ala Gly Asp Phe Trp Gly Gly Ala Gly Ser Val Ala Cys Gln
            275                 280                 285

Glu Phe Ile Thr Gln Leu Gly Arg Asn Phe Gln Val Ile Tyr Glu Gln
290                 295                 300

Ala Asn Ala His Gly Gln Lys Val Gln Ala Ala Gly Asn Asn Met Ala
305                 310                 315                 320

Gln Thr Asp Ser Ala Val Gly Ser Ser Trp Ala
                325                 330

<210> SEQ ID NO 5
<211> LENGTH: 3
<212> TYPE: PRT
<213> ORGANISM: Artificial Sequence
<220> FEATURE:
<223> OTHER INFORMATION: Description of Artificial Sequence:flexible
      polylinker

<400> SEQUENCE: 5

Gly Cys Gly
 1
```

```
<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence:flexible
      polylinker

<400> SEQUENCE: 6

Gly Cys Gly Gly Cys Gly
  1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence:flexible
      polylinker

<400> SEQUENCE: 7

Gly Cys Gly Gly Cys Gly Gly Cys Gly
  1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence:flexible
      polylinker

<400> SEQUENCE: 8

Gly Gly Gly Gly Ser
  1               5

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence:flexible
      polylinker

<400> SEQUENCE: 9

Gly Gly Gly Gly Ser Gly Gly Gly Gly Ser
  1               5                  10

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence:flexible
      polylinker

<400> SEQUENCE: 10

Gly Gly Gly Gly Ser Gly Gly Gly Gly Ser Gly Gly Gly Gly Ser
  1               5                  10                  15
```